US012749557B2

(12) United States Patent
Lee et al.

(10) Patent No.: US 12,749,557 B2
(45) Date of Patent: Sep. 29, 2026

(54) METHODS AND SYSTEMS FOR IMPROVED K-MER STORAGE AND RETRIEVAL

(71) Applicant: The Board of Trustees of the Leland Stanford Junior University, Stanford, CA (US)

(72) Inventors: HoJoon Lee, Palo Alto, CA (US); Hanlee P. Ji, Stanford, CA (US); Tsachy Weissman, Stanford, CA (US); Dmitri Pavlichin, Redwood City, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 1094 days.

(21) Appl. No.: 17/754,017

(22) PCT Filed: Sep. 21, 2020

(86) PCT No.: PCT/US2020/051852
§ 371 (c)(1),
(2) Date: Mar. 21, 2022

(87) PCT Pub. No.: WO2021/055972
PCT Pub. Date: Mar. 25, 2021

(65) Prior Publication Data

US 2023/0230657 A1 Jul. 20, 2023

Related U.S. Application Data

(60) Provisional application No. 62/903,351, filed on Sep. 20, 2019.

(51) Int. Cl.
*G16B 30/00* (2019.01)
*G06F 3/06* (2006.01)
(Continued)

(52) U.S. Cl.
CPC .......... *G16B 30/00* (2019.02); *G06F 3/0604* (2013.01); *G06F 3/0655* (2013.01);
(Continued)

(58) Field of Classification Search
CPC ........ G16B 30/00; G16B 20/40; G16B 45/00; G16B 50/00; G16B 30/10; G16B 50/30;
(Continued)

(56) References Cited

U.S. PATENT DOCUMENTS 8,116,988 B2 2/2012 Glick et al.
2009/0270277 A1* 10/2009 Glick .................... G16B 30/00 506/8
(Continued)

FOREIGN PATENT DOCUMENTS

EP 4031677 A1 7/2022
WO WO-2011073680 A1 * 6/2011 ............ G16B 30/10
(Continued)

OTHER PUBLICATIONS

Takenaka, Yoichi, Shigeto Seno, and Hideo Matsuda. "Perfect Hamming code with a hash table for faster genome mapping." BMC genomics 12.Suppl 3 (2011): S8. (Year: 2011).*
(Continued)

*Primary Examiner* — Jesse P Frumkin
(74) *Attorney, Agent, or Firm* — KPPB LLP

(57) ABSTRACT

Systems and methods of storing and retrieving K-mer data in a data structure are provided. In certain embodiments, the K-mer data is stored as an integer value that defines an address of a slot in the data structure. In many embodiments, each slot in the data structure stores the remaining portion of the K-mer that is not part of the prefix. Additional embodiments are directed to genetic or genomic analysis using a data structure for storing K-mer data.

17 Claims, 19 Drawing Sheets

Specification includes a Sequence Listing.

(51) Int. Cl.
*G06F 16/22* (2019.01)
*G16B 20/40* (2019.01)
*G16B 45/00* (2019.01)
*G16B 50/00* (2019.01)
*G16B 50/30* (2019.01)

(52) U.S. Cl.
CPC ........ *G06F 3/0673* (2013.01); *G06F 16/2255* (2019.01); *G16B 20/40* (2019.02); *G16B 45/00* (2019.02); *G16B 50/00* (2019.02); *G16B 50/30* (2019.02)

(58) Field of Classification Search
CPC .... G06F 3/0604; G06F 3/0655; G06F 3/0673; C12Q 1/6869
See application file for complete search history.

(56) References Cited

U.S. PATENT DOCUMENTS

| | | | |
|---|---|---|---|
| 2011/0257889 A1 | 10/2011 | Klammer et al. | |
| 2015/0057947 A1 | 2/2015 | Drmanac et al. | |
| 2015/0331619 A1* | 11/2015 | Zheng | G06F 16/2255 711/154 |
| 2016/0259880 A1 | 9/2016 | Semenyuk | |
| 2017/0169159 A1* | 6/2017 | Sazonov | G16B 30/00 |
| 2018/0181708 A1 | 6/2018 | Van Rooyen et al. | |
| 2023/0282309 A1* | 9/2023 | Zhao | G16B 30/10 702/19 |

FOREIGN PATENT DOCUMENTS

| | | |
|---|---|---|
| WO | 2018007034 A1 | 1/2018 |
| WO | 2021055972 A1 | 3/2021 |

OTHER PUBLICATIONS

Liu, Jinlin, Qiang Chen, and Chen Zhang. "K-mer index of DNA sequence based on hash algorithm." International Journal on Computational Science & Applications (IJCSA) 5.4 (2015): 19-28. (Year: 2015).*
Pan, Tony, et al. "Kmerind: A flexible parallel library for k-mer indexing of biological sequences on distributed memory systems." Proceedings of the 7th ACM international conference on bioinformatics, computational biology, and health informatics. 2016. (Year: 2016).*
Mohamadi, Hamid, et al. "ntHash: recursive nucleotide hashing." Bioinformatics 32.22 (2016): 3492-3494. (Year: 2016).*
Pan, Tony C., Sanchit Misra, and Srinivas Aluru. "Optimizing high performance distributed memory parallel hash tables for DNA k-mer counting." SC18: International Conference for High Performance Computing, Networking, Storage and Analysis. IEEE, 2018. (Year: 2018).*
Carpov, Sergiu, and Thibaud Tortech. "Secure top most significant genome variants search: iDASH 2017 competition." BMC medical genomics 11.Suppl 4 (2018): 82. (Year: 2018).*
Chen, Mei, et al. "A fast retrieval algorithm based on fibonacci hashing for audio fingerprinting systems." 2013 International Conference on Advanced Information Engineering and Education Science (ICAIEES 2013). Atlantis Press, 2013. (Year: 2013).*
Martínez-Prieto, Miguel A., et al. "Practical compressed string dictionaries." Information Systems 56 (2016): 73-108. (Year: 2016).*
International Preliminary Report on Patentability for International Application PCT/US2020/051852, Report issued Mar. 15, 2022, Mailed on Mar. 31, 2022, 06 Pgs.
International Search Report and Written Opinion for International Application No. PCT/US2020/051852, Search completed Dec. 13, 2020, Mailed Jan. 28, 2021, 11 Pgs.
"BBDuk Guide", printed Feb. 8, 2022 from https://jgi.doe.gov/data-and-tools/bbtools/bb-tools-user-guide/bbduk-guide, 6 pgs.
Abo et al., "BreaKmer: detection of structural variation in targeted massively parallel sequencing data using kmers", Nucleic Acids Research, Feb. 18, 2015, vol. 43, Issue 3, e19, pp. 1-13, https://doi.org/10.1093/nar/gku1211.
Ames et al., "Design and Optimization of a Metagenomics Analysis Workflow for NVRAM", IEEE International Parallel & Distributed Processing Symposium Workshops, May 19, 2014, pp. 556-565.
Cover et al., "Elements of Information Theory", Wiley, Oct. 17, 2006, 397 pgs.
Deorowicz et al., "Kmer-db: instant evolutionary distance estimation", bioRxiv preprint doi: https://doi.org/10.1101/263590; this version posted Feb. 12, 2018, 2 pgs.
Dobin et al., "STAR: ultrafast universal RNA-seq aligner", Bioinformatics, Jan. 1, 2013, vol. 29, No. 1, pp. 15-21, Advance Access publication Oct. 25, 2012, doi: 10.109./bioinformatics/bts635.
Hopmans et al., "A programmable method for massively parallel targeted sequencing", Nucleic Acids Res 2014, 42 (10):e88, 16 pgs.
Kokot et al., "KMC 3: counting and manipulating k-mer statistics", Bioinformatics, 2017, vol. 33, No. 17, pp. 2759-2761, doi: 10.1093/bioinformatics/btx304.
Lek et al., "Analysis of protein-coding genetic variation in 60,706 humans", Nature, Aug. 17, 2016, vol. 536, pp. 285-291, doi:10.1038/nature 19057.
Li et al., "Fast and accurate short read alignment with Burrows-Wheeler transform", Bioinformatics, May 18, 2009, vol. 25, No. 14, pp. 1754-1760, doi:10.1093/bioinformatics/btp324.
Liu et al., "A novel data structure to support ultra-fast taxonomic classification of metagenomic sequences with k-mer signatures", Bioinformatics, Jan. 1, 2018, vol. 34, No. 1, pp. 171-178, doi: 10.1093/bioinformatics/btx432.
Marcais et al., "A fast, lock-free approach for efficient parallel counting of occurrences of k-mers", Bioinformatics, vol. 27, No. 6, Mar. 15, 2011, pp. 764-770.
McKenna et al., "The Genome Analysis Toolkit: A MapReduce framework for analyzing next-generation DNA sequencing data", Genome Research, Jul. 12, 2010, vol. 20, pp. 1297-1303, http://www.genome.org/cgi/doi/10.1101/gr.107524.110.
Rosenfeld et al., "Limitations of the human reference genome for personalized genomics", PLoS One 2012, 7(7):e40294, 9 pgs.
Zhang et al., "These are not the k-mers you are looking for: efficient online k-mer counting using a probabilistic data structure", arXiv: 1309.2975v4 [q-bio.GN], Jul. 14, 2014, 22 pgs., doi: 10.1371/journal.pone.0101271.

* cited by examiner

| GGGCACCACCACACTATCTT | #mismatches | locations |
|---|---|---|
| ..............A..... | 1 | chr4:94007930-94007949 |
| .................G.C | 2 | chr17:7674874-7674893 |
| ..............A....A | 2 | chr11:78472870-78472889 |
| .............A...T.. | 2 | chr16:54310841-54310860 |
| ...A.............T.. | 2 | chr15:38380875-38380894 |

| 30-mer | SRR 6000890 | SRR 6000891 | SRR 6000892 | SRR 6000893 | SRR 6000894 | SRR 6000895 |
|---|---|---|---|---|---|---|
| AAAAAAAAAAAAAAAAAAAAAAAAAAAAAA | 255 | 255 | 255 | 255 | 255 | 255 |
| CCCTTGCCGTAGTTGAAGCTGATGATGGGA | 0 | 0 | 2 | 0 | 0 | 0 |
| CCTTGCCGTAGTTGAAGCTGATGATGGGAA | 0 | 0 | 2 | 0 | 0 | 0 |
| ATAATCCAGGCTCAGCCTTTGCAGATTGAC | 0 | 0 | 4 | 4 | 0 | 0 |
| AACCGCTGCATTTGGCTATAGGGGCAATCG | 0 | 0 | 12 | 0 | 0 | 0 |
| AATTGTTTGTAAGGTTATTGTTTCTGGTGT | 0 | 0 | 0 | 0 | 0 | 2 |
| AATCAGTTCCTAAGACCTCGAATAATTCTT | 16 | 8 | 10 | 19 | 24 | 15 |
| TCTCTTCTTTACTGAATCGACGGTGCCGAC | 0 | 0 | 0 | 6 | 0 | 0 |
| TAATCCAGGCTCAGCCTTTGCAGATTGACA | 0 | 0 | 4 | 4 | 0 | 0 |
| CAATGATGCTATGAACAACAAAAAGATTTC | 0 | 2 | 0 | 17 | 17 | 0 |
| CCCTCGCGAGGGGATACGAGCTGAAGTACA | 0 | 3 | 0 | 0 | 0 | 0 |
| ... | | | | | | |

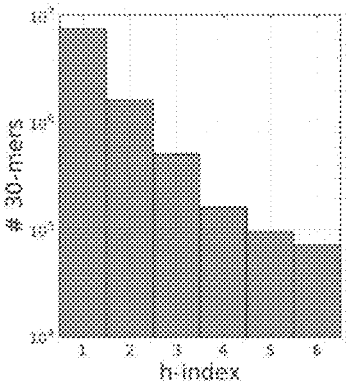

FIG. 11

Expected counts of k-mers from 50X coverage with 100% tumor purity

| K-mer type | Wildtype k-mer counts | | Neo k-mer counts | | % of neo k-mers |
|---|---|---|---|---|---|
| | Normal | Tumor | Normal | Tumor | |
| | 50 | 25 | 0 | 25 | 50 |
| | 100 | 75 | 0 | 25 | 20 |
| | 500 | 475 | 0 | 25 | 5 |

| Kmer | Total # of Distinct Kmers | # of Unique Kmers | % of Unique Kmers |
|---|---|---|---|
| 15 | 333,996,502 | 85,790,147 | 25.67% |
| 19 | 2,070,184,390 | 1,876,537,416 | 90.65% |
| 20 | 2,189,055,410 | 2,054,549,187 | 93.86% |
| 21 | 2,253,936,484 | 2,145,382,413 | 95.18% |
| 25 | 2,381,753,574 | 2,296,150,198 | 96.41% |
| 30 | 2,482,044,850 | 2,404,680,033 | 96.88% |
| 40 | 2,615,555,800 | 2,549,848,669 | 97.49% |
| 50 | 2,697,532,516 | 2,641,304,762 | 97.92% |
| 100 | 2,819,184,505 | 2,785,097,132 | 98.80% |

```
SEQUENCE LISTING


<160> NUMBER OF SEQ ID NOS: 37

<210> SEQ ID NO 1
<211> LENGTH: 10
<212> TYPE: DNA
<213> ORGANISM: artificial sequence
<220> FEATURE:
<223> OTHER INFORMATION: example sequence from figure 1

<400> SEQUENCE: 1

ttgggaaact                                                          10


<210> SEQ ID NO 2
<211> LENGTH: 11
<212> TYPE: DNA
<213> ORGANISM: artificial sequence
<220> FEATURE:
<223> OTHER INFORMATION: example sequence from figure 2

<400> SEQUENCE: 2

ttgggaaact a                                                        11


<210> SEQ ID NO 3
<211> LENGTH: 10
<212> TYPE: DNA
<213> ORGANISM: artificial sequence
<220> FEATURE:
<223> OTHER INFORMATION: example sequence from figure 2

<400> SEQUENCE: 3

gcctttaaag                                                          10


<210> SEQ ID NO 4
<211> LENGTH: 20
<212> TYPE: DNA
<213> ORGANISM: artificial sequence
<220> FEATURE:
<223> OTHER INFORMATION: example sequence from figure 9a

<400> SEQUENCE: 4

gggcaccacc acactatctt                                               20


<210> SEQ ID NO 5
<211> LENGTH: 20
<212> TYPE: DNA
<213> ORGANISM: homo sapiens
```

<400> SEQUENCE: 5
acaattggct tggcaggttg 20

<210> SEQ ID NO 6
<211> LENGTH: 20
<212> TYPE: DNA
<213> ORGANISM: homo sapiens

<400> SEQUENCE: 6
caattggctt ggcaggttga 20

<210> SEQ ID NO 7
<211> LENGTH: 20
<212> TYPE: DNA
<213> ORGANISM: homo sapiens

<400> SEQUENCE: 7
aattggcttg gcaggttgaa 20

<210> SEQ ID NO 8
<211> LENGTH: 20
<212> TYPE: DNA
<213> ORGANISM: homo sapiens

<400> SEQUENCE: 8
attggcttgg caggttgaat 20

<210> SEQ ID NO 9
<211> LENGTH: 20
<212> TYPE: DNA
<213> ORGANISM: homo sapiens

<400> SEQUENCE: 9
ttggcttggc aggttgaatt 20

<210> SEQ ID NO 10
<211> LENGTH: 20
<212> TYPE: DNA
<213> ORGANISM: homo sapiens

<400> SEQUENCE: 10
tggcttggca ggttgaattt 20

<210> SEQ ID NO 11
<211> LENGTH: 20
<212> TYPE: DNA
<213> ORGANISM: homo sapiens

<400> SEQUENCE: 11
ggcttggcag gttgaatttg 20

<210> SEQ ID NO 12
<211> LENGTH: 20
<212> TYPE: DNA
<213> ORGANISM: homo sapiens

<400> SEQUENCE: 12
gcttggcagg ttgaatttga 20

<210> SEQ ID NO 13
<211> LENGTH: 20
<212> TYPE: DNA

<213> ORGANISM: homo sapiens

<400> SEQUENCE: 13
cttggcaggt tgaatttgac 20

<210> SEQ ID NO 14
<211> LENGTH: 20
<212> TYPE: DNA
<213> ORGANISM: homo sapiens

<400> SEQUENCE: 14
ttggcaggtt gaatttgacc 20

<210> SEQ ID NO 15
<211> LENGTH: 20
<212> TYPE: DNA
<213> ORGANISM: homo sapiens

<400> SEQUENCE: 15
tggcaggttg aatttgaccc 20

<210> SEQ ID NO 16
<211> LENGTH: 20
<212> TYPE: DNA
<213> ORGANISM: homo sapiens

<400> SEQUENCE: 16
ggcaggttga atttgacccg 20

<210> SEQ ID NO 17
<211> LENGTH: 20
<212> TYPE: DNA
<213> ORGANISM: homo sapiens

<400> SEQUENCE: 17
gcaggttgaa tttgacccga 20

<210> SEQ ID NO 18
<211> LENGTH: 30
<212> TYPE: DNA
<213> ORGANISM: Artificial Sequence
<220> FEATURE:
<223> OTHER INFORMATION: example sequence from figure 10a

<400> SEQUENCE: 18
ggttccaata ccagtcagca gcagcagcag 30

<210> SEQ ID NO 19
<211> LENGTH: 34
<212> TYPE: DNA
<213> ORGANISM: artificial sequence
<220> FEATURE:
<223> OTHER INFORMATION: example sequence from figure 10a

<400> SEQUENCE: 19
cagcagcagc agcagcccca cgcagtcgtg gggg 34

<210> SEQ ID NO 20
<211> LENGTH: 30
<212> TYPE: DNA
<213> ORGANISM: artificial sequence
<220> FEATURE:
<223> OTHER INFORMATION: example sequence from figure 11

<400> SEQUENCE: 20

```
aaaaaaaaaa aaaaaaaaaa aaaaaaaaaa                                        30


<210> SEQ ID NO 21
<211> LENGTH: 30
<212> TYPE: DNA
<213> ORGANISM: artificial sequence
<220> FEATURE:
<223> OTHER INFORMATION: example sequence from figure 11

<400> SEQUENCE: 21

cccttgccgt agttgaagct gatgatggga                                        30


<210> SEQ ID NO 22
<211> LENGTH: 30
<212> TYPE: DNA
<213> ORGANISM: artificial sequence
<220> FEATURE:
<223> OTHER INFORMATION: example sequence from figure 11

<400> SEQUENCE: 22

ccttgccgta tttgaagctg atgatgggaa                                        30


<210> SEQ ID NO 23
<211> LENGTH: 30
<212> TYPE: DNA
<213> ORGANISM: artificial sequenc
<220> FEATURE:
<223> OTHER INFORMATION: example sequence from figure 11

<400> SEQUENCE: 23

ataatccagg ctcagccttt gcagattgac                                        30


<210> SEQ ID NO 24
<211> LENGTH: 30
<212> TYPE: DNA
<213> ORGANISM: artificial sequence
<220> FEATURE:
<223> OTHER INFORMATION: example sequence from figure 11

<400> SEQUENCE: 24

aaccgctgca tttggctata ggggcaatcg                                        30


<210> SEQ ID NO 25
<211> LENGTH: 30
<212> TYPE: DNA
<213> ORGANISM: artificial sequence
<220> FEATURE:
<223> OTHER INFORMATION: example sequence from figure 11

<400> SEQUENCE: 25

aattgtttgt aaggttattg tttctggtgt                                        30


<210> SEQ ID NO 26
<211> LENGTH: 30
<212> TYPE: DNA
<213> ORGANISM: artificial sequence
<220> FEATURE:
<223> OTHER INFORMATION: example sequence from figure 11

<400> SEQUENCE: 26

aatcagttcc taagacctcg aataattctt                                        30


<210> SEQ ID NO 27
<211> LENGTH: 30
<212> TYPE: DNA
```

<213> ORGANISM: artificial sequence
<220> FEATURE:
<223> OTHER INFORMATION: example sequence from figure 11

<400> SEQUENCE: 27
tctcttcttt actgaatcga cggtgccgac 30

<210> SEQ ID NO 28
<211> LENGTH: 30
<212> TYPE: DNA
<213> ORGANISM: artificial sequence
<220> FEATURE:
<223> OTHER INFORMATION: example sequence from figure 11

<400> SEQUENCE: 28
taatccaggc tcagcctttg cagattgaca 30

<210> SEQ ID NO 29
<211> LENGTH: 30
<212> TYPE: DNA
<213> ORGANISM: artificial sequence
<220> FEATURE:
<223> OTHER INFORMATION: example sequence from figure 11

<400> SEQUENCE: 29
caatgatgct atgaacaaca aaaagatttc 30

<210> SEQ ID NO 30
<211> LENGTH: 30
<212> TYPE: DNA
<213> ORGANISM: artificial sequence
<220> FEATURE:
<223> OTHER INFORMATION: example sequence from figure 11

<400> SEQUENCE: 30
ccctcgcgag gggatacgag ctgaagtaca 30

<210> SEQ ID NO 31
<211> LENGTH: 20
<212> TYPE: DNA
<213> ORGANISM: homo sapiens

<400> SEQUENCE: 31
tttgggaaac ctttaaaggg 20

<210> SEQ ID NO 32
<211> LENGTH: 20
<212> TYPE: DNA
<213> ORGANISM: homo sapiens

<400> SEQUENCE: 32
tgctttcata ctaggcaccc 20

<210> SEQ ID NO 33
<211> LENGTH: 19
<212> TYPE: DNA
<213> ORGANISM: artificial sequence
<220> FEATURE:
<223> OTHER INFORMATION: example sequence from figure 13a

<400> SEQUENCE: 33
tagctgatcg tagctgatc 19

<210> SEQ ID NO 34
<211> LENGTH: 19

```
<212> TYPE: DNA
<213> ORGANISM: artificial sequence
<220> FEATURE:
<223> OTHER INFORMATION: example sequence from figure 13a

<400> SEQUENCE: 34

tagctgatct tagctgatc                                               19


<210> SEQ ID NO 35
<211> LENGTH: 10
<212> TYPE: DNA
<213> ORGANISM: artificial sequence
<220> FEATURE:
<223> OTHER INFORMATION: example sequence from figure 2

<400> SEQUENCE: 35

tgggaaacta                                                         10


<210> SEQ ID NO 36
<211> LENGTH: 30
<212> TYPE: DNA
<213> ORGANISM: artificial sequence
<220> FEATURE:
<223> OTHER INFORMATION: example sequence from figure 11

<400> SEQUENCE: 36

ccttgccgta gttgaagctg atgatgggaa                                   30


<210> SEQ ID NO 37
<211> LENGTH: 17
<212> TYPE: DNA
<213> ORGANISM: artificial sequence
<220> FEATURE:
<223> OTHER INFORMATION: example sequence from figure 2

<400> SEQUENCE: 37

ttgggaaacc tttaaag                                                 17
```

METHODS AND SYSTEMS FOR IMPROVED K-MER STORAGE AND RETRIEVAL

CROSS-REFERENCE TO RELATED APPLICATIONS

This application is a national stage of PCT Patent Application No. PCT/US2020/051852, entitled "Methods and Systems for Improved K-mer Storage and Retrieval," filed Sep. 21, 2020, which claims priority to U.S. Provisional Patent Application No. 62/903,351 entitled "Methods and Systems for Improved K-mer Storage and Retrieval," filed Sep. 20, 2019, the disclosures of which are incorporated herein by reference.

STATEMENT REGARDING FEDERALLY SPONSORED RESEARCH OR DEVELOPMENT

This invention was made with Governmental support under Grant No. HG000205 awarded by the National Institutes of Health. The government has certain rights in the invention.

FIELD OF THE INVENTION

The present disclosure is directed to methods and systems for storing and retrieving various types of information; and more particularly to methods and systems for storing and retrieving K-mer data using a novel data structure.

SEQUENCE LISTING

This application hereby incorporates by reference the material of the electronic Sequence Listing filed concurrently herewith. The material in the electronic Sequence Listing is submitted as a text (.txt) file entitled "06228_PCT Seq_List_ST25.txt" created on Oct. 16, 2020, which has a file size of approximately 6 KB, and is herein incorporated by reference in its entirety.

BACKGROUND

Next generation sequencing (NGS) has accelerated biomedical genomics research and clinical genetic assessment of disease-related genetic variation. The analysis of NGS sequence data involves mapping and annotation of genetic variation. These processes require high quality human genome assemblies as a reference. Considering the structural complexity and sheer diversity of human genomes, the current static reference lacks the features and contextual flexibility to represent the breadth of human variation. As a result, critical features of individual genomes are practically missed or may contain errors due to the limitations of a static reference. To date there is no effective and comprehensive representation of multiple human genome assemblies and genomic variations at the population level although such data has been available for some time. Recent expansion of population genome sequencing projects are harbingers that there is significantly more to come with a deluge of whole genome sequencing soon to arrive in the coming years. In particular, it remains a challenge to characterize the structural variations at the population level on the basis of the genomic coordinates since the start and end locations vary among individuals.

BRIEF SUMMARY

The present disclosure provides embodiments directed to systems and methods for storing and retrieving genetic data in the form of K-mers in data structures.

In one embodiment, a method for indexing K-mers includes obtaining a nucleotide sequence, defining a K-mer size, and indexing K-mers in the nucleotide sequence according to the K-mer size, where the K-mers are stored in a data structure defined by a plurality of slots, and where each slot has an address and stores data, the address is defined by a prefix portion of each K-mer, and the slot stores the remaining portion of the K-mer sequence.

In a further embodiment, the prefix portion of each K-mer is defined as a quotient upon division by a parameter plus a number not exceeding a maximum number of hash collisions.

In another embodiment, the parameter is integer-valued, and each slot stores an invertible function of the remainder of a K-mer upon division by the integer-valued parameter.

In a still further embodiment, the parameter is integer-valued, and the number is an integer h between 0 and J, where J equals one less maximum number of hash collisions, and each slot stores an invertible function of the remainder of a K-mer upon division by the integer-valued parameter and h.

In still another embodiment, the data structure further includes metadata associated with each K-mer stored therein.

In a yet further embodiment, the metadata comprises at least one of the following: source, population, species, date of acquisition, sequencing platform, data type, and identity of the sample.

In yet another embodiment, the method further includes updating the data structure with additional sequence data.

In a further embodiment again, the updating step is accomplished by obtaining additional sequence data and indexing K-mers in the additional sequence data according to the K-mer size, where the K-mers are stored in the data structure.

In another embodiment again, the nucleotide sequence is a whole genome sequence.

In a further additional embodiment, the nucleotide sequence is a human reference sequence.

In another additional embodiment, the K-mer size is 11-150 base pairs.

In a still yet further embodiment, each K-mer is stored as a binary integer representing of the underlying DNA sequence of each K-mer.

In still yet another embodiment, the K-mers are converted to generate a more uniform distribution.

In a still further embodiment again, the conversion is accomplished by multiplying each K-mer by u (mod B), where B is a table size of the data structure, and u is any number with no common divisors with B.

In still another embodiment again, the method further includes retrieving at least one K-mer from the data structure.

In a still further additional embodiment, the retrieved K-mer is unhashed from the data structure by multiplying each K-mer by v(mod B), where v*u*x=x(mod B), where x represents the binary integer representing the underlying DNA sequence of the K-mer.

In still another additional embodiment, collisions occurring during the indexing step are handled by scanning to a lower order slot and incrementing the integer value of the remaining portion of the K-mer by a value equal to a difference between the prefix and the lower order slot.

In a yet further embodiment again, a maximum number of hash collisions results in data being stored in another data structure.

In yet another embodiment again, a data structure for storing genetic or genomic data includes a plurality of memory slots and a plurality of K-mers, wherein each memory slot is associated with an address, wherein each K-mer is stored in a specific memory slot based on an integer value of a prefix of the K-mer, and the remaining portion of the K-mer is stored in the memory slot.

In a yet further additional embodiment, the data structure further stores metadata associated with each K-mer in the plurality of K-mers, and wherein the metadata is stored in a position associated with the slot where the K-mer is stored.

In yet another additional embodiment, the metadata comprises at least one of the following: source, population, species, date of acquisition, sequencing platform, data type, and identity of the sample.

In a further additional embodiment again, the K-mers are converted to generate a more uniform distribution.

In another additional embodiment again, the conversion is accomplished by multiplying each K-mer by u(mod B), where B is a table size of the data structure, and u is any number with no common divisors with B.

In a still yet further embodiment again, the K-mer is unhashed from the data structure by multiplying the K-mer by v(mod B), where v*u*x=x(mod B), where x represents the binary integer representing the underlying DNA sequence of the K-mer.

In still yet another embodiment again, collisions occurring when the K-mer is stored is handled by scanning to a lower order slot and incrementing the integer value of the remaining portion of the K-mer by a value equal to a difference between the prefix and the lower order slot.

In a still yet further additional embodiment, a maximum number of hash collisions results in data being stored in another data structure.

In still yet another additional embodiment, a method to identify genomic events includes accessing a data structure, wherein the data structure comprises a plurality of memory slots and a plurality of K-mers, where each memory slot is associated with an address, where each K-mer is stored in a specific memory slot based on an integer value of a prefix of the K-mer, and the remaining portion of the K-mer is stored in the memory slot, querying the data structure to obtain a set of K-mers associated with a genomic event, and outputting the set of K-mers associated with the genomic event.

In a yet further additional embodiment again, the data structure further stores metadata associated with each K-mer in the plurality of K-mers, and wherein the metadata is stored in a position associated with the slot where the K-mer is stored.

In yet another additional embodiment again, the querying the data structure further obtains metadata associated with the K-mers associated with the genomic event.

In a still yet further additional embodiment again, the method further includes outputting the metadata associated with the K-mers associated with the genomic event.

In still yet another additional embodiment again, the genomic event is a short variant, and the set of K-mers represents all K-mers overlapping the short variant.

In another further embodiment, the short variant is a single nucleotide polymorphism or an indel.

In still another further embodiment, the genomic event is a structural variant, and the set of K-mers represents all K-mers overlapping the structural variant. In yet another further embodiment, the structural variant is selected from the group consisting of: a fusion event, a tandem repeat, and a copy number variant.

In another further embodiment again, the genomic event is a sequence of interest, and the set of K-mers represents all K-mers overlapping the sequence of interest.

Another further additional embodiment, the sequence of interest is selected from the group consisting of: a gene, a transcription site, and a protospacer adjacent motif.

In yet another additional embodiment, the method further includes querying the data structure for a second time to obtain a second set of K-mers associated with a second genomic event and outputting the second set of K-mers associated with the second genomic event.

In a further yet additional embodiment, the second genomic event is a haplotype defined by K-mers associated with the first genomic event, and the second set of K-mers represents variants identified by the first set of K-mers.

Additional embodiments and features are set forth in part in the description that follows, and in part will become apparent to those skilled in the art upon examination of the specification or may be learned by the practice of the invention. A further understanding of the nature and advantages of the present invention may be realized by reference to the remaining portions of the specification and the drawings, which forms a part of this disclosure.

BRIEF DESCRIPTION OF THE DRAWINGS

The description will be more fully understood with reference to the following figures and data graphs, which are presented as various embodiments of the disclosure and should not be construed as a complete recitation of the scope of the disclosure, wherein:

FIG. 11 illustrates counts and a histogram of the number of K-mers from six individual genome samples that exist in all six samples in accordance with various embodiments.

DETAILED DESCRIPTION

Figure 1A:
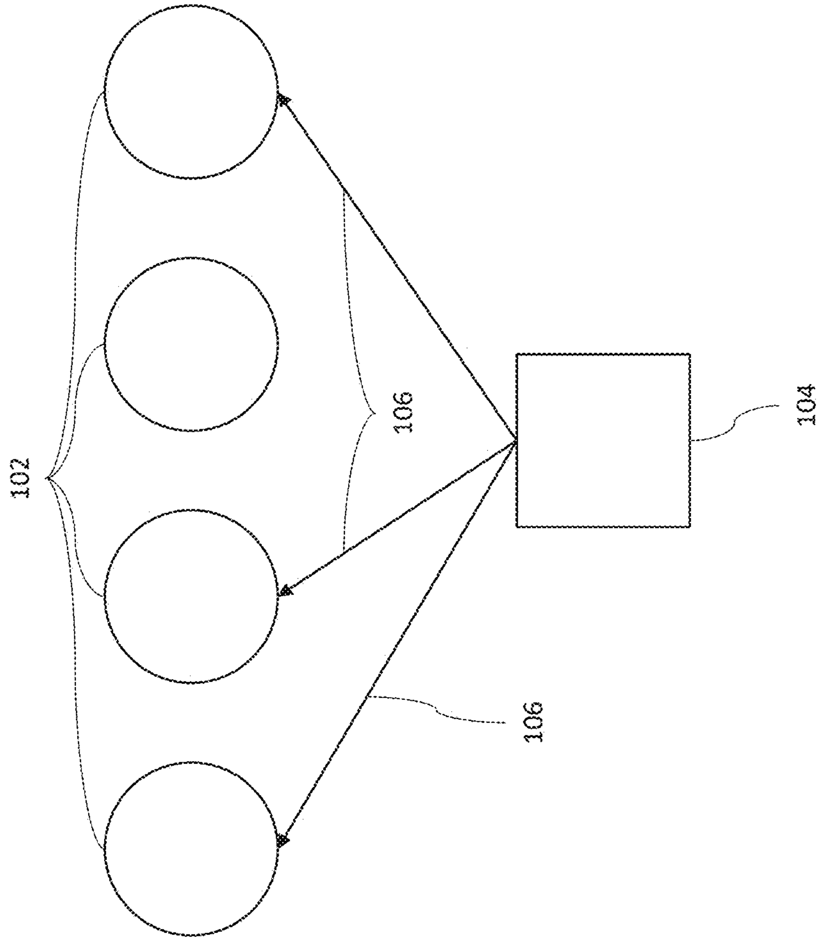
FIGS. 1A-1C illustrate K-mer and variant correlations in accordance with various embodiments.

The present disclosure may be understood by reference to the following detailed description, taken in conjunction with the drawings as described below. It is noted that, for purposes of illustrative clarity, certain elements in various drawings may not be drawn to scale.

In accordance with the provided disclosure and drawings, systems and methods of storing and retrieving genetic data in the form of K-mers are provided. Several embodiments are directed to a data structure for storing K-mer data, while additional embodiments are directed to storing and/or retrieving K-mer data in a data structure.

The human genome reference sequence has been instrumental for biomedical investigation, advances in understanding the molecular basis of disease, and clinical translation of genomic discoveries. Without the reference, the analysis of countless genomes and the billions of sequence reads associated with it would have been difficult if not impossible. The most popular genomic analysis tools such as BWA, GATK, and STAR are dependent on the reference genome. (See Mckenna A, et al: The Genome Analysis Toolkit: a MapReduce framework for analyzing next-generation DNA sequencing data. Genome Res 2010, 20 (9): 1297-1303; Li H & Durbin R: Fast and accurate short read alignment with Burrows-Wheeler transform Bioinformatics 2009, 25 (14): 1754-1760; Dobin A, et al. STAR: ultrafast universal RNA-seq aligner. Bioinformatics 2013, 29 (1): 15-21; the disclosures of which are incorporated herein by reference in their entirety.) Further, many large sequencing projects such as The Cancer Genome Atlas (TCGA) have reported all identified cancer genetic alterations according to the current human reference, GRCh38. To date, the reference human genome has played critical role in biomedical research and will continue to be important as we transition genome-based precision medicine.

However, the current human genome reference has dramatic limitations due to its static linear presentation. (See Rosenfeld J A, et al.: Limitations of the human reference genome for personalized genomics. PLOS One 2012, 7 (7): e40294; the disclosure of which is incorporated herein by reference in its entirety.) Since the Human Genome Project's original release, new assemblies are being developed. Further, current state-of-the-art sequencing technologies have characterized huge amounts of genetic variation in human populations and this number will quickly expand in the near future. Citing an example, the Genome Aggregation Database (gnomAD) have already reported 260,570,577 variants with their allelic presentation at the population level-seven ethnic groups—from 125,748 whole exomes and 15,708 whole genomes. (See Lek M, et al.: Analysis of protein-coding genetic variation in 60,706 humans. Nature 2016, 536 (7616): 285-291; the disclosure of which is incorporated herein by reference in its entirety.) This information has not been fully incorporated into the current human reference-its static framework is too restricted provide these features efficiently. In addition, the current reference is a compilation of several individuals, and therefore has limited information about the diploid and structural characteristics of human genomes as relayed by haplotype segments and annotation of structural variations (SVs). More detailed variant phasing information across long contiguous segments of the genome is now attainable through state-of-the-art sequencing technologies; such information is already yielding important insights into inheritance, evolution, disease, and more. It is critical to fully utilize these new type of sequencing data given their importance and increasing use in all future genome sequencing studies.

K-mers are short segments of sequence of that have intrinsic advantages for computational sequencing analysis and are increasingly being used in genomic studies. Certain embodiments described herein provide a K-mer-based indexing strategy and/or computational architecture to encode and annotate large collections of genomes. Such architectures can seamlessly link the pan-genome reference to population data and have dramatic advantages in terms of computational speed and storage space as well. Additional embodiments provide systems, such as a web interface portal, to provide a K-mer-based index that enables an individual, such as a researcher, to query and analyze genomic data against known variants, including single nucleotide variants (SNVs), such as variants identified in gnomAD and/or COSMIC. Numerous embodiments promote pan-genome index without much difficulties and with the expectation that lots of human genome sequencing and assembly will be generated through state-of-the-art technologies as well as considerations of cost and ease.

K-mer representations of genomic sequences are common in genomic data analysis and are appealing in their conceptual simplicity. That being said, there remains an enormous potential for K-mer-based indexing to become a new standard for representing genomic variation. This approach has many advantages in respect to large collections of genomes rather than a single reference genome. K-mers make natural keys for a database, but their prior use has been tied to particular applications: tools exist for counting K-mers, read filtering, evolutionary distance estimation, and much more. (See Marcais G & Kingsford C: A fast, lock-free approach for efficient parallel counting of occurrences of k-mers. Bioinformatics 2011, 27 (6): 764-770; Kokot M, Dlugosz M, Deorowicz S: KMC 3: counting and manipulating k-mer statistics, Bioinformatics 2017, 33 (17): 2759-2761; BBDuk Guide [jgi.doe.gov/data-and-tools/bbtools/bb-tools-user-guide/bbduk-guide/]; and Deorowicz S, et al.: Kmer-db: instant evolutionary distance estimation. Bioinformatics 2019, 35 (1): 133-136; the disclosures of which are incorporated herein by reference in their entirety.) K-mers further enable the representation of variation in a way that is not tied to a specific reference genome. Also, K-mers can handle structural variations as naturally as SNVs, whereby a structural variation is presented by the collection of K-mers that it contains rather than by a genome-specific coordinate. Several embodiments expand the utilities of K-mer analysis by associating K-mer keys with metadata such as a genomic coordinate in a fasta record, a count within a fastq file, an identifier denoting the dataset of origin when indexing multiple genomes jointly, and/or a flag denoting a privacy setting.

Figure 1B:
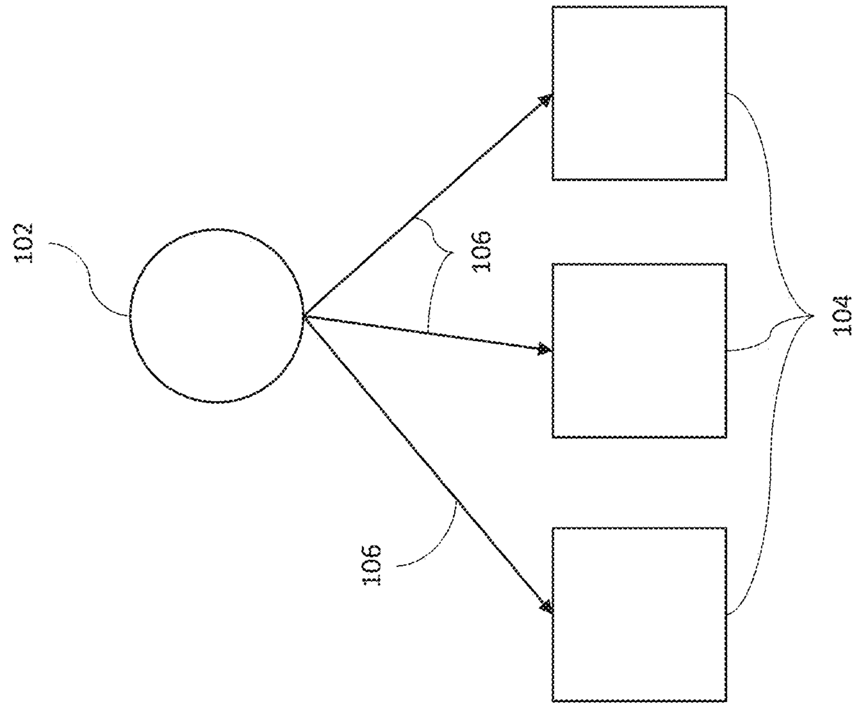
Figure 1C:
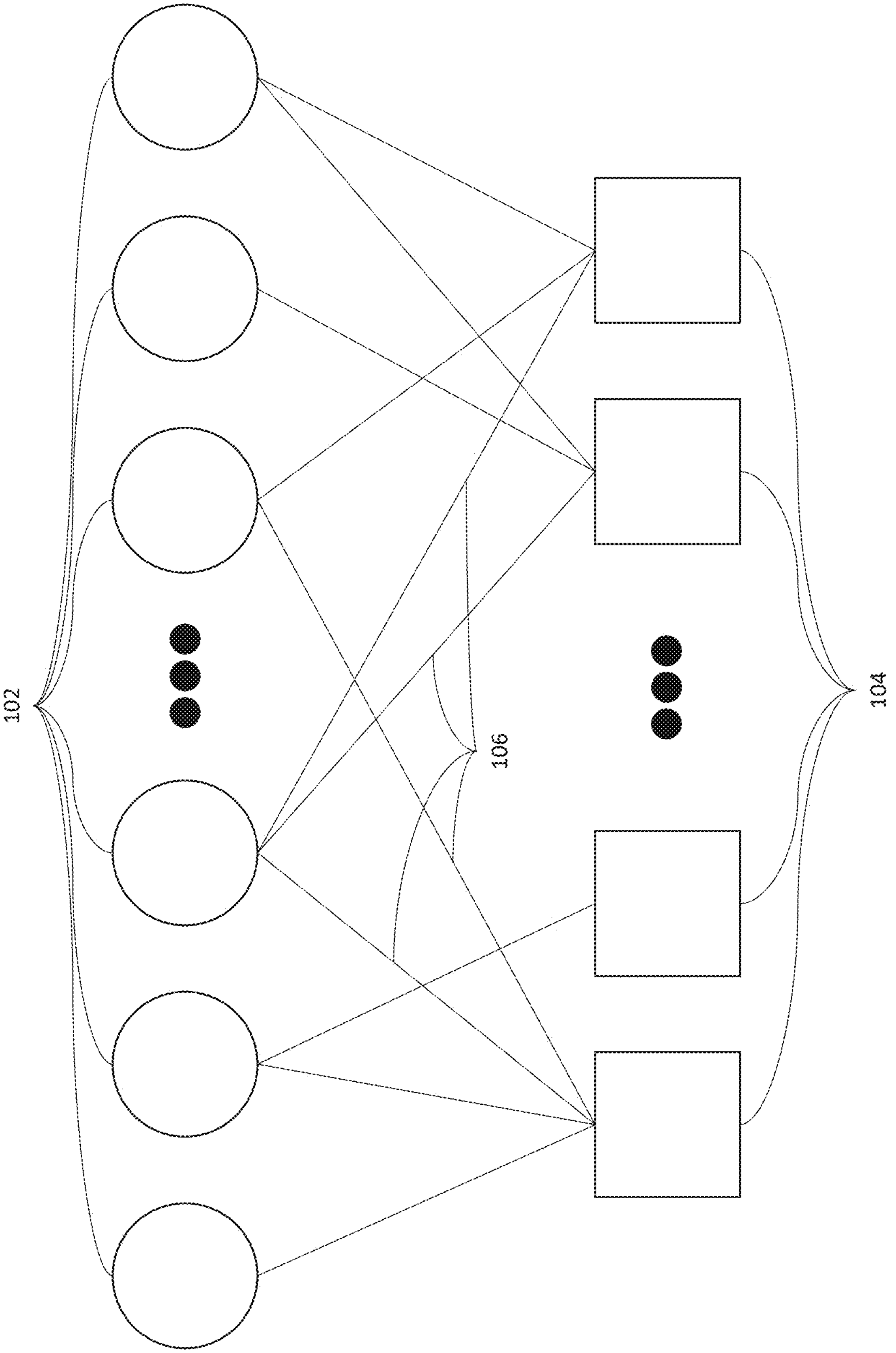

Turning to FIGS. 1A-1C, a challenge in genomics is untethering the description of variants from the global coordinate system of a reference genome while preserving enough local context information to position the variant in any particular genome. The description should enable interpretation across many genomes (e.g. deletion of the third exon of TP53). To address these challenges, certain embodiments model variants as collections of K-mers together with metadata, borrowing heavily from the idea of factor graphs in probabilistic modeling. There are two basic entities—K-mers 102 and variants 104—the term "variant" is broad, including single nucleotide variants (SNVs), single nucleotide polymorphisms (SNPs), structural variations, insertions or deletions (indels), contigs only present in a particular reference, and haplotypes. Edges 106 in the graph connect K-mers with the variants that contain them. FIG. 1A shows an example of an embodiment, where a single variant 104 is present in multiple K-mers 102, while FIG. 1B illustrates an example where a single K-mer represents multiple variants. In sum, the collection of K-mers and variants grow into a collection of hundreds of billions of K-mers with representing hundreds of millions variants across multiple reference genomes, as illustrated in FIG. 1C, which illustrates a bipartite factor graph for a collection of variants from multiple reference genomes.

Various embodiments associate certain data with K-mer data. The data associate with particular K-mers includes (but not limited to) locations, counts, origin datasets, variants, population statistics, tags, flags (e.g., privacy setting flags), and/or any other data that may be relevant to K-mers and projects involving K-mers.

Figure 2:
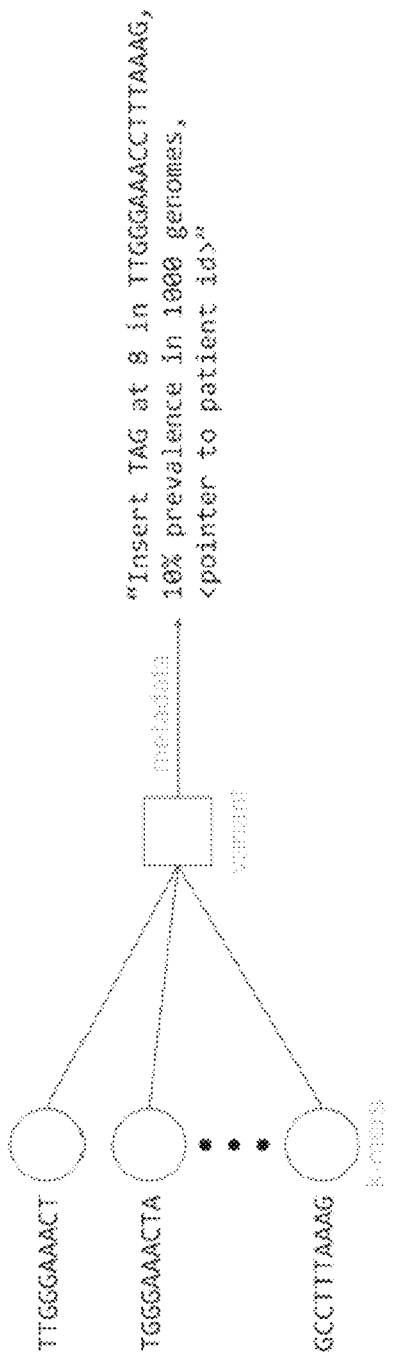
FIG. 2 illustrates a small structural variant associated with K-mers in accordance with various embodiments.

Turning to FIG. 2 as an example, a short insertion with respect to one reference genome might correspond to the VCF record (e.g., #CHROM: 20, POS: 10000, REF: C, ALT: CTAG). In factor graph frameworks of some embodiments (FIG. 2), this short insertion would correspond to a variant node pointing to all of the K-mer nodes spanning this insertion. The variant node would also contain important metadata identifying the variant as an insertion along with its prevalence in a particular population, dataset of origin, and mapping coordinate in one or more reference genomes (i.e. pan-genome assemblies). As a result, k is sufficiently large that the leftmost and rightmost K-mers map this variant to a unique position in a given assembly with high probability, or establish the presence of this variant in FASTQ data.

Figure 3:
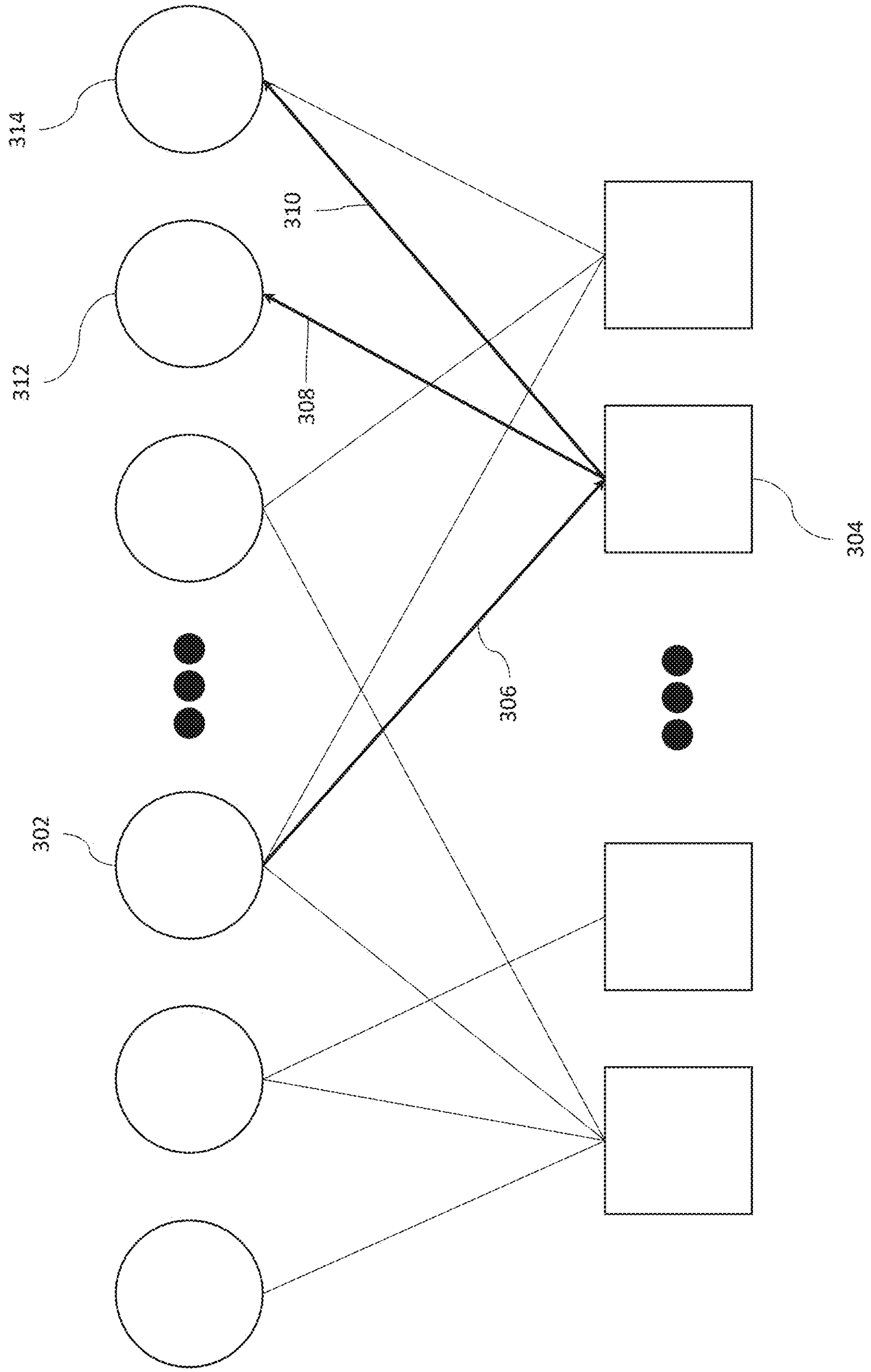
FIG. 3 illustrates a bipartite factor graph in accordance with various embodiments.

In many embodiments, a factor graph representation of pan-genomic variation supports fast computation on the set of variants in the graph in a way that is scalable to billions of nodes and extensible to include novel classes of variants contributed by other groups. One graph structure application involves rapidly determining the presence or absence of a variant in a novel genome (or even in an unassembled sequencing sample). Turning to FIG. 3, a bipartite factor graph in accordance with some embodiments is illustrated. In FIG. 3, upon observation of a K-mer 302 in a novel genome, some embodiments traverse an edge 306 to discover variant 304. Certain embodiments traverse edges 308, 310 to identify whether K-mers 312, 314 are also in the novel genome to confirm the presence of variant 304. To traverse this graph in the K-mer-to-variant direction, several embodiments follow the edges explicitly encoded in a K-mer-indexed database. Edges in the reverse direction of variant-to-K-mer are implicit from the metadata associated with the variant, and can be generated on-demand rather than stored on disk.

Developing a K-Mer Data Structure

Figure 4A:
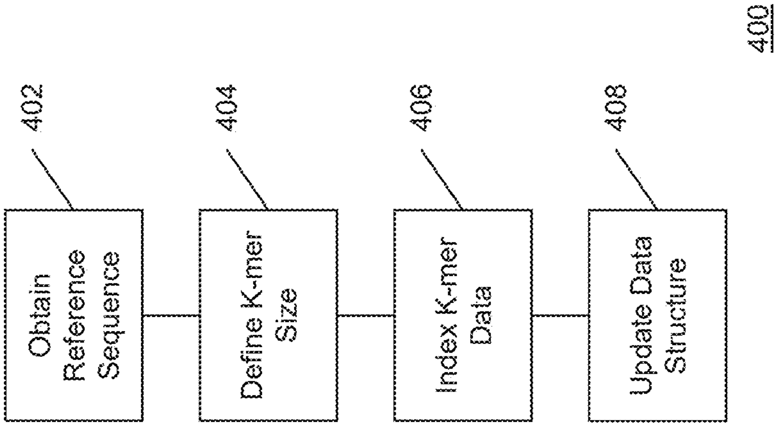
FIG. 4A illustrates a method of indexing K-mers in accordance with various embodiments.

Turning to FIG. 4, certain embodiments are directed to methods for indexing K-mers, such as Method 400. In method 400, an input sequence is obtained at 402. The input sequence can be nearly any type of sequence data, such as any sequence with a finite alphabet, where a fixed length can be defined. Many embodiments index nucleic acid sequence (e.g., four base pairs—A,C,T,G), while additional embodiments focus on indexing peptide sequences (e.g., twenty amino acids). The input sequence can be generated anew or received as a sequence file. In numerous embodiments, the sequence is received as a file, such as in FASTA, FASTQ, BED, VCF, and/or any other format describing genetic and/or genomic sequences. In many embodiments, the reference is a genome sequenced and/or assembled custom for a species of interest, such as plant, mammal, or any other species. In certain embodiments, the input sequence is publicly available through resources, such as the Department of Energy, Department of Agriculture, a public institution or public research project, and/or any other available genome sequence. In additional embodiments, the sequence is generated using a sequencer or sequencing platform, including Illumina platforms, Ion Torrent platforms, Roche 454 platforms, PacBio platforms, ABI platforms (including the 3700 and related platforms and SOLID platforms), and/or any other sequencing platform or combination of sequencing platforms. In embodiments where the sequence is obtained anew, the sequence may further be assembled into a genome build, contigs, chromosomes, and/or any other larger organization of DNA greater than individual reads.

At 404, a K-mer size is defined. The K-mer size is defined based on the wishes of an individual for their specific purpose of use. As such, the K-mer size can be defined as any integer from 1 to the total number of bases in a genome. Typically, K-mers are defined with a size of between 1 and 150 base pairs. In some embodiments, K-mer size is set to 11 base pairs to fit with a small sequencing reads. In some embodiments, if an individual desires K-mers comparable in size for PCR primers, they may define K-mer size to be in the range of 20-25 base pairs in length. In additional embodiments, the K-mer size is defined to be greater than 35-50 base pairs in length. Certain embodiments may maximize computer processing to keep K-mer size at or below 64 base pairs, representing 128 bits, which fits into a processor register. Some embodiments allow a user to define a range of K-mers, such that the method creates multiple indexes, where each index with a different K-mer size.

Once a K-mer size is defined, certain embodiments of method 400 index K-mer data in a data structure at 406. Indexing in accordance with various embodiments is based on concepts drawn from K-mer techniques developed in Jellyfish, KMC, and other available K-mer tools but is updated. (See e.g., Hopmans E S, et al.: A programmable method for massively parallel targeted sequencing. Nucleic Acids Res 2014, 42 (10): e88.) However, numerous embodiments s utilize previously unexploited convenient mathematical facts, is designed to make efficient use of memory caching. Indexing methodologies used in many embodiments are described elsewhere herein.

A number of embodiments further update the data structure at 408. Updating a data structure can include novel K-mers, such as K-mers derived from ongoing sequencing efforts, including population sequencing efforts, (e.g., gnomAD). By updating the index, the data structure of certain embodiments includes population variation data and/or any additional data generated from the novel sequencing input. In several embodiments that update the data structure with novel information, the data structure includes metadata identifying the data, such as source, population, species, date of acquisition, sequencing platform, data type, identity of the sample, and/or any other relevant information.

When updating the data structure, some embodiments receive the additional sequence as assembled sequences, such as those described above, while other embodiments receive additional sequence in the form of variant files (e.g., variant call files (VCF)). When receiving additional sequence as a set of variants, the positions of the variants can be leveraged to identify the underlying genomic sequence based on metadata that is present in the data structure for the reference sequence, then complete the full K-mer sequence and store any novel K-mers in the data structure and/or update the existing metadata in the system to identify the source and/or location of the K-mers in the data structure.

It should be noted that the method above can be run on a computing device capable of the complex operations described and capable of processing the amount of data generated by or from genomic sequence and/or sequencing. As such, some embodiments are directed to non-transitory, machine-readable media containing instructions to direct a processor to perform the method or methods as described above. Modifications to the embodiments allows for different processes to complete, including memory mapping, multiple threads, and/or Bloom filters. Memory mapping allows for a user to decrease the amount of memory used for K-mer indexing to run at the expense of run time.

Figure 4B:
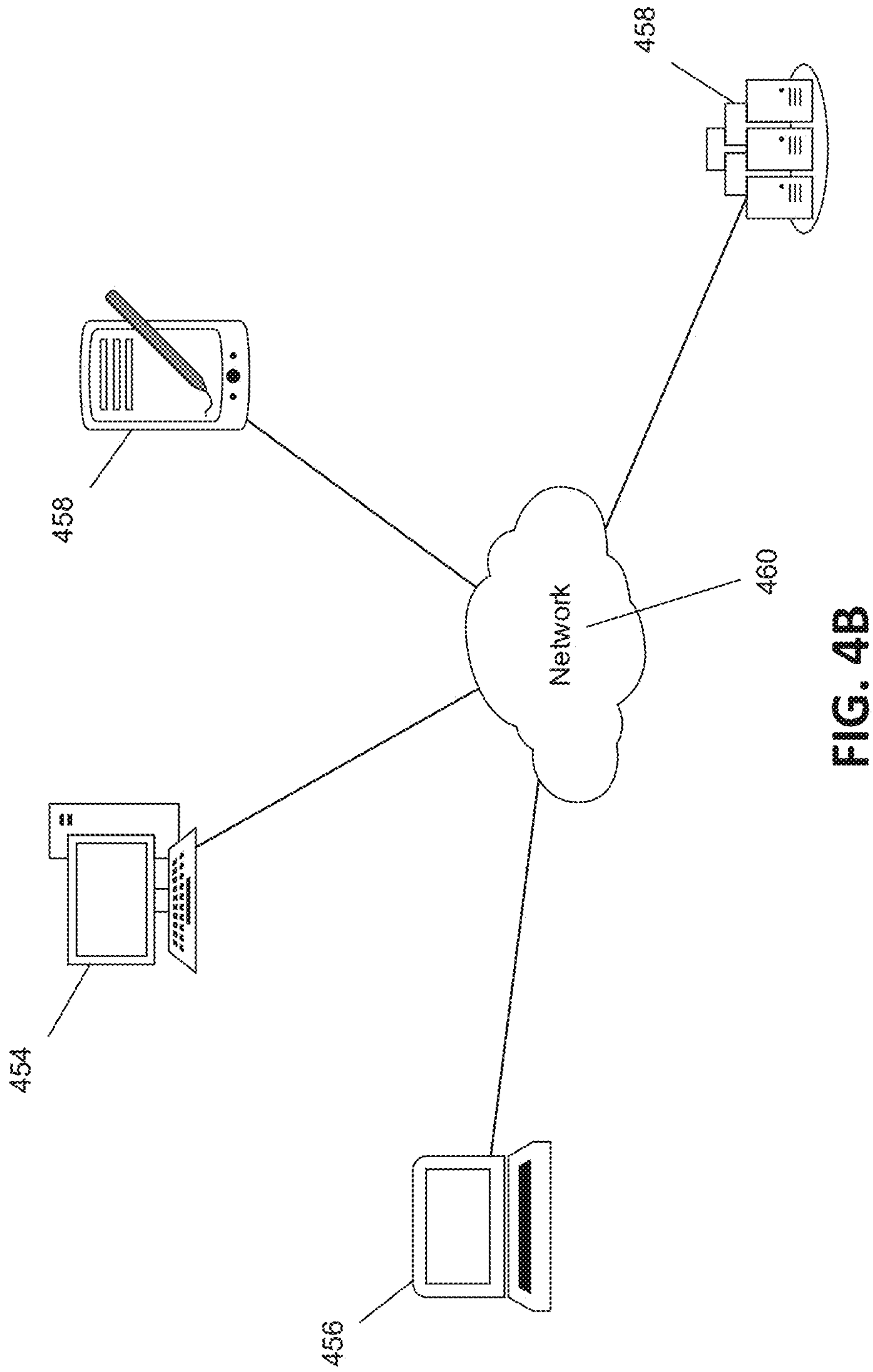
FIG. 4B illustrates a network diagram of computing devices including a networked server in accordance with various embodiments.

Additionally, certain embodiments are directed to systems capable of operating the functions as described above. Turning to FIG. 4B, various embodiments are capable of operating on a computing device, such as a server 452, a personal computer 454, a laptop 456, a tablet 458, or other computing device. Various embodiments are implemented over a network such that a data structure is housed on a remote server 452 or device connected via a network 460. In a networked configuration, one or more users can use a computing device (e.g., personal computer 454, laptop 456, tablet 458) to update or query the data structure located on server 452, where updating can be accomplished by selecting specific genomic data or data located on the server and/or transmitting genomic data over network 460 to server 452.

Indexing K-Mers

The approach to indexing is as follows: Embodiments represent a K-mer by the last 2k bits of a 64-bit integer (i.e., k≤32; where A corresponds to 00, C corresponds to 01, etc.). As such, an example of a 31-mer in some embodiments would look like:

1001110110011011111111010011010111111011011010101 011001100111111

The 31-mer occupies one slot in a data structure with B slots, then the first $\log_2(B)$ bits of the K-mer is the address in the table of the K-mer, since this number of bits is how many bits it takes to describe the index of a slot in the table. Thus, the address is defined by the underlined portion (referred to as prefix):

1001110110011011111111010011010111111011011010101 011001100111111

Figure 5A:
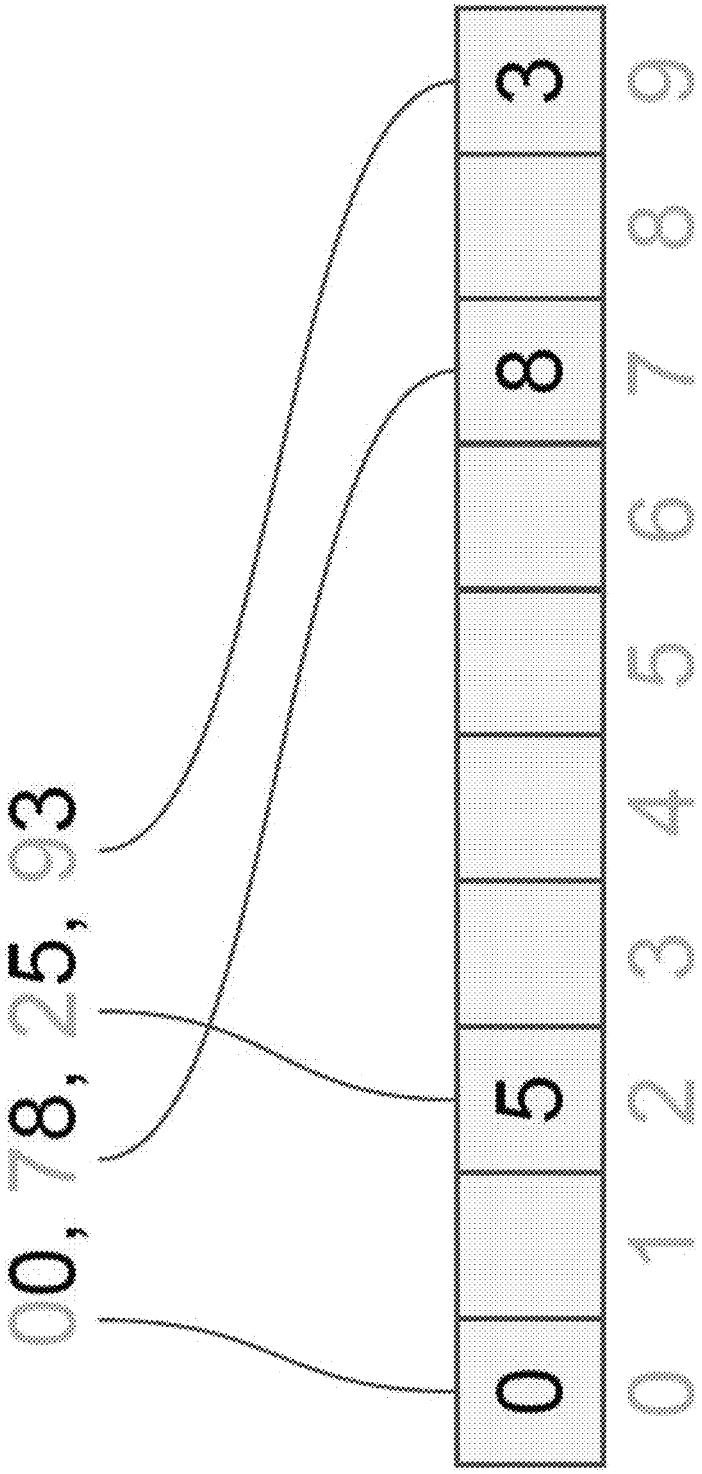
FIGS. 5A-5B illustrate how K-mers are indexed in a data structure in accordance with various embodiments.
Figure 5B:
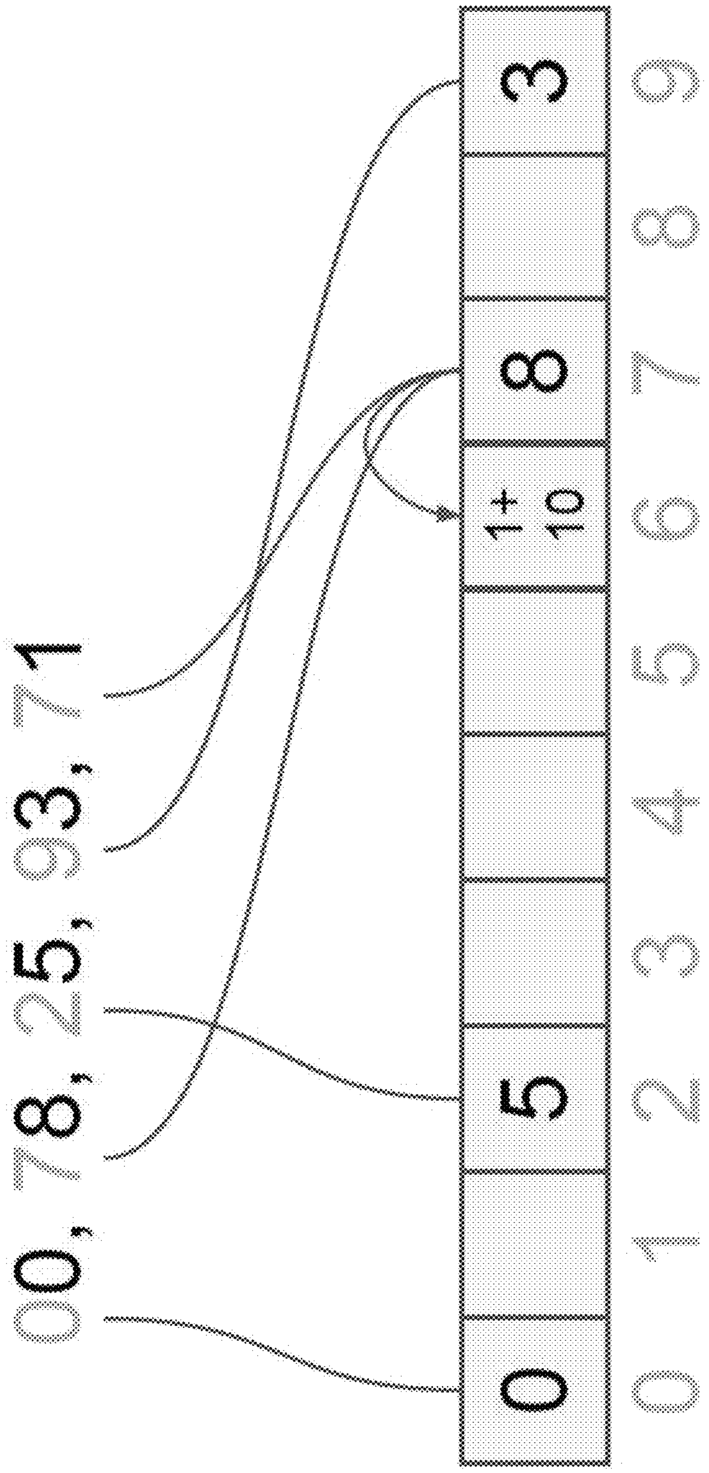

The remaining bits (not underlined) are stored in the corresponding data structure slot. To simplify the explanation of the data structure in accordance with embodiments, instead of a size-4 alphabet ("ACGT"), the following example uses a size-10 alphabet ("0123456789") and k=2. In certain embodiments, the address is defined as a quotient of the prefix and/or prefix of a quotient of the K-mer, a quotient upon division by a parameter, and/or a quotient upon division by a parameter plus a number not exceeding a maximum number of hash collisions, such as will be described below. A K Turning to FIGS. 5A-5B, an embodiment of a data structure storing 2-mers 00, 78, 25, and 93 is illustrated. In these embodiments, the first character of the 2-mer is the slot address, which stores the second character, so integer 0 is stored in slot 0, integer 5 is stored in slot 2, etc. FIG. 5B illustrates how embodiments handles collisions while storing K-mers—e.g., linear hash-collision resolution. Thus, when the 2-mer 71 is added to the list of K-mers, this 2-mer would typically be stored in slot 7, which already represents the 2-mer 78. As shown in FIG. 5B, some embodiments scan left (arrow) until an available slot is identified. The contents of the slot are incremented by 10 to compensate for the reduced slot address. Additional embodiments scan right and decrement by 10, while certain embodiments employ strategies to scan both left and right (and increment or decrement according to which direction used), which may increase the likelihood of identifying an empty slot closer to the address initially identified by the K-mer. In many embodiments, to reconstruct a K-mer stored in the data structure, the address of the slot is concatenated to the contents of the slot. For example, if the contents of slot 2 is the integer 5, the resultant K-mer is 25. By resolving K-mer collisions by scanning to one direction to find the nearest open slot, K-mers that caused a collision are placed closer to its expected address. By placing a K-mer in proximity to its expected address, many embodiments capitalize on the memory access protocols of computing systems, which typically access a block of slots rather than accessing a single slot at a time. By accessing a block of slots in the data structure, computing systems typically access the slot of the collided K-mer, even though it is not in its expected location. This phenomenon prevents computing systems from having to access multiple locations of memory in an attempt to find or locate the expected K-mer.

Figure 6:
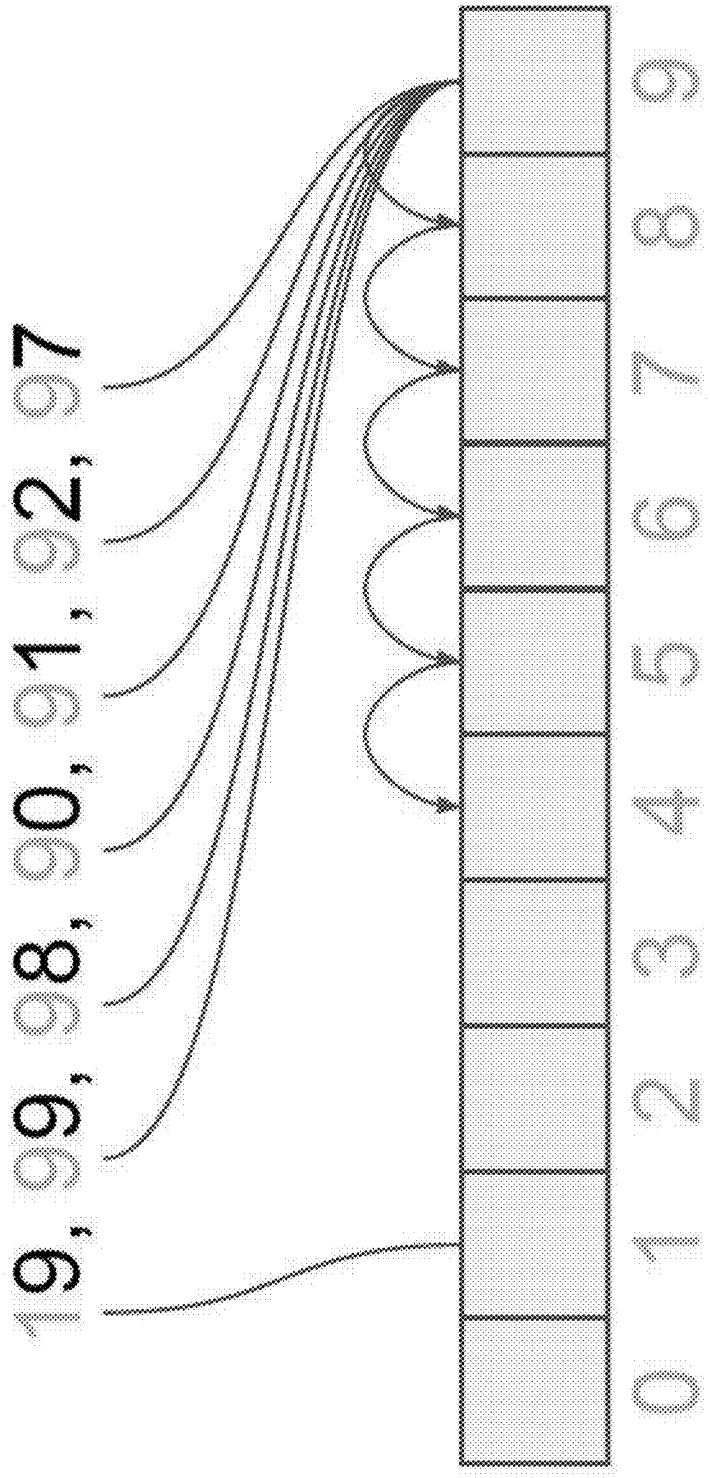
FIG. 6 illustrates how systems and methods handle hash collisions in accordance with various embodiments.
Figure 7:
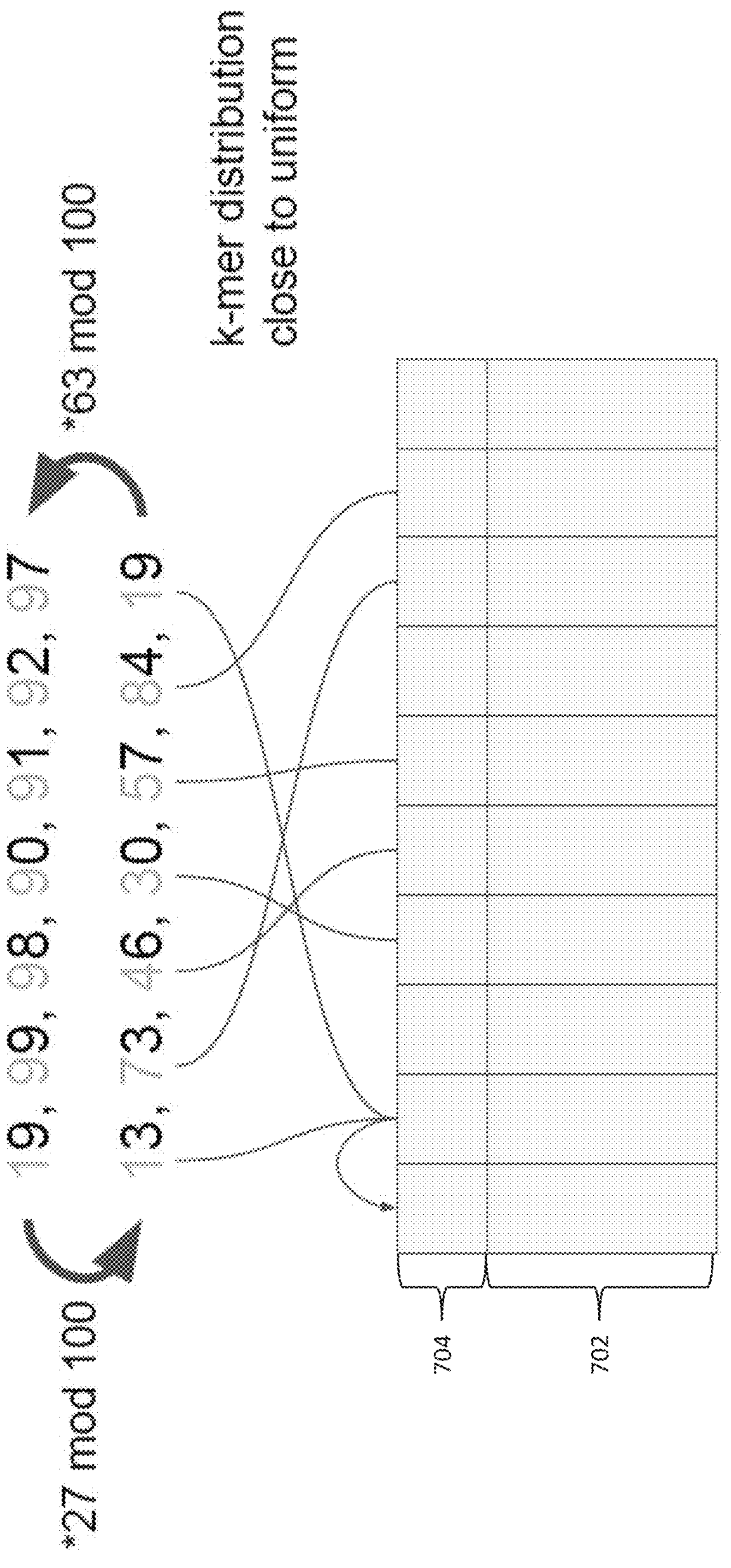
FIG. 7 illustrates a how systems and methods create a more uniform distribution of K-mers in a data structure in accordance with various embodiments.

A potential issue that arises is when many K-mers have the same prefix, which results in many collisions when storing K-mers in the data structure, as illustrated in FIG. 6. This situation occurs commonly in genomic sequences, for example, when many K-mers begin with AAAA . . . A. In FIG. 6, multiple K-mers possess the prefix 9, which results in numerous scans left to identify open slots in the data structure. To overcome this issue, many embodiments distribute of K-mers more uniform to prevent "clumping" of many K-mers in the same slot. To generate a uniform distribution of K-mers, instead of storing K-mer x represented as a 64-bit integer, some embodiments store K-mers utilizing a Fibonacci hash function. Fibonacci hash functions allow for a single multiplication and binary "and" operation, e.g., the integer u*x(mod B), where u is any number with no common divisors with the table size B. Thanks to Bezout's identity and the extended Euclidean algorithm, a number v can always be found such that v*(u*x)=x (mod B); that is, multiplication by v inverts ("unhashes") multiplication by u. Both the hashing and unhashing operations were highly efficient, corresponding to a single integer multiplication. Hashing efficiency can be even higher if B is a power of the alphabet size, since then the mod operation can be computed via bit shifting. An example of this is illustrated in FIG. 7, where the K-mers are converted using *27 (mod 100), then stored. To reconstruct the K-mer, the converted data is multiplied by 63 (mod 100). As noted above, a K-mer can be defined in a numerical format based on the size of the alphabet. For example, a nucleic acid sequence possesses alphabet, X={A,C,G,T} and size of alphabet, |X|=4; which can be represented numerically as the digits 1-4 or in binary as 00, 01, 10, and 11. As such, a K-mer is viewed as an integer in the set {0,1, . . . , ($|X^k|-1$}. Additionally, all arithmetic operations on K-mers (e.g., addition, subtraction, division, multiplication, remainder) are performed modulo $|X^k|$.

However, certain embodiments allow duplicates, such that a data structure can have multiple copies of the same key in the data structure. Additional embodiments possess a sorting function, such that the entries are in the hash table are sorted in hash order of the data structure.

As also shown in FIG. 7, many embodiments also store metadata 702 associated with each indexed K-mer 704. By associating metadata 702, many embodiments allow users to build novel analysis tools and visualizations on top of a more basic data structure presented elsewhere herein. For example, a preliminary implementation of a data structure in accordance with embodiments as a K-mer counter (i.e., the metadata is an integer count), the embodiment showed by 4-fold speed increase over the popular software Jellyfish, which is dedicated to the task of K-mer counting. Moreover, data structure of some embodiments permitted constant expected time querying of a single K-mer (with around 1 million randomly selected 30-mers queried per second for GRCh38), a feature that is not currently available in any K-mer counting software. Further, since the first few bits of a K-mer determine its address in data structures of some embodiments, the K-mers are always sorted, enabling comparisons of K-mer indices built for different collections of genomes. These observations render embodiments as a scalable and fast method of K-mer-based indexing.

As the pan-genome grows in size, so will the set of all K-mers it contains, so it is of increasing importance to keep all data structures as compact as possible. K-mer indexes in accordance with many embodiments are designed to be maximally compact, while supporting efficient query operations. Considering the following counting argument that draws from the principles of data compression in information theory: (See Cover T M & Thomas J A: Elements of information theory, 2d ed. Hoboken, N.J.: Wiley-Interscience; 2006; the disclosure of which is incorporated herein by reference in its entirety.) Suppose that N K-mers uniformly randomly sampled from all $4^k$ possible K-mers. The necessary number of bits is $\log_2(C(4^k,N))$ where C(m,n) is the binomial coefficient "m choose n." Now using Stirling's approximation (assuming that $4^k$ is much larger than N), one can rewrite this quantity as $\log_2(C(4^k,N))\approx N(2k-\log_2(N))$, or $2k-\log_2(N)$ bits per K-mer. Numerous embodiments of data structures uses B buckets, where B is chosen so that the table is perhaps about 75% full, so that B=N/0.75, so $\log_2(B)$ bits per K-mer are implicit from a K-mer's address in the data structure, and so some embodiments use $2k\text{-}\log_2(N/0.75)\approx 2k\ \log_2(N)+0.42$ bits per K-mer. This is about 0.42 bits per K-mer worse than optimal. If certain embodiments permit at most h=32 hash collisions before declaring a K-mer unhashable and moving it to an overflow table, then the extra cost rises by $\log_2(h)=5$ bits per K-mer over the optimal amount of space used. This cost comes at the benefit of nearly constant-time querying of K-mers.

A combination of Fibonacci hashing and linear hash collision resolution provide many improvements in computer functionality over prior methods. For example, the hash function and its inverse are computable using a single multiplication and binary "and" operation. Additionally, a linear hash collision resolution reduces the number of expensive memory cache misses (e.g., for in-memory operation) and expensive page loads from disk (e.g., for memory mapped operation). Further, a combination allows for near constant-time random access, where time is proportional to the expected number of hash reprobes per key.

Additionally, the hashing strategy used in many embodiments allows the K-mer table to remain sorted on its K-mer keys, which enables fast, multithreaded operations involving multiple K-mer tables, such as unions, intersections, complements, etc. Additionally, with this sorting, queries can be performed faster, since sorting information can be used to terminate queries early.

An additional improvement in space and memory is accomplished in many embodiments by using part of a K-mer as the K-mer key, thus reducing in half the number of bits to be stored in a data structure. Because less data will need to be read and written, computing time is reduced to construct and query a data structure.

Capabilities of Various Embodiments

Figure 8:
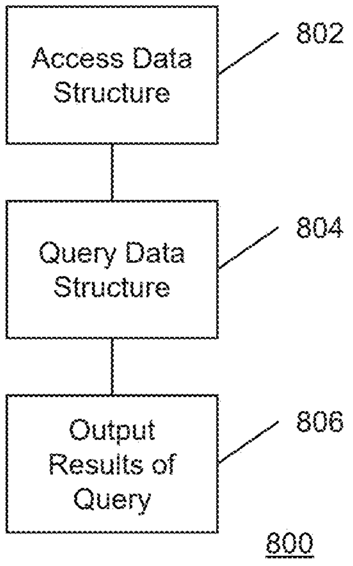
FIG. 8 illustrates a method of querying a data structure containing K-mer data in accordance with various embodiments.

Turning to FIG. 8, method 800 describes methods of using a data structure of many embodiments for applied genomic uses. In particular, at 802, many embodiments access a data structure containing K-mers generated from genomic data. In certain embodiments, accessing the data structure involves generating or building a data structure through means described elsewhere herein. In some embodiments, the data structure is located remotely and is accessed via a network connection. In additional embodiments, the data structure is obtained from a source, such as from downloading it from a remote device to possess locally. Various embodiments combine multiple methods for accessing a data structure, such as by obtaining a pre-generated data structure and updating it with additional data or by generating a novel data structure located remotely. In certain embodiments, the data structure contains K-mer data from a single genome, while certain embodiments contain K-mer data from more than one genome. For example, certain embodiments contain K-mer data from population data (e.g., 1000 Genomes Project).

At 804, various embodiments query the data structure. In certain embodiments, querying is accomplished by querying for a genomic event, where genomic events include short variants (e.g., single nucleotide polymorphisms (SNPs), indels, etc.), structural variants (e.g., a fusion event, a tandem repeat, and a copy number variant, etc.), or a sequence of interest (e.g., a gene, a transcription site, or a protospacer adjacent motif (PAM), etc.). In certain instances, the query is identified as a specific nucleotide sequence (e.g., a 2-mer, a 3-mer, a 4-mer, a 5-mer, a 6-mer, a 7-mer, an 8-mer, a 9-mer, a 10-mer, a 12-mer, a 15-mer, a 20-mer, a 25-mer, a 30-mer, a 35-mer, a 40-mer, a 50-mer, a 55-mer, a 60-mer, a 65-mer, a 70-mer, a 75-mer, a 100-mer, a 150-mer, etc.) In some embodiments, the query is performed by searching information located in metadata associated with the indexed K-mers.

At 806, additional embodiments output the results of the query. In certain embodiments, the output is a list of K-mers with associated details, such as number of mismatches, genome source(s), increase in K-mer count, and any other information that is present in the data structure or can be calculated or identified by the information therein.

For example, systems and methods as described herein, users are able to compute statistics across collections of genomes or primary sequencing files, including, but not limited to, one or more of the following:

1) given a K-mer data structure constructed for multiple complete genomes (e.g., VCF files, primary sequencing files, etc.), compute population-wide queries on K-mer content (e.g., return all K-mers occurring at least twice in a particular genome but zero times in every other indexed genome);
2) given a K-mer data structure, compute population-wide queries on variant content (e.g. return all variants that occur in at least 1% of samples and at most 10% of samples in 1000 Genomes);

3) constructing a scatter plot for comparing pairs of genomes or primary sequencing files, or multiple 2-D scatterplot projections when comparing more than two genomes jointly;
4) the ability to select visually or programmatically a region of interest for the K-mers it contains, outputting any associated metadata, like clinical significance, for any previously indexed variants associated with K-mers in the region of interest, and storing the output in a human-readable format, along with metadata permitting others to repeat the same analysis steps.

Additional functionality of some embodiments includes, but is not limited to, one or more of the following:

1) Given multiple primary sequencing data files (e.g., FASTQ files), identify all K-mers statistically overrepresented in one sample relative to another ("neo K-mers"), thus likely containing a variant.
2) Given a collection of neo K-mers, overlap them into small contiguous sequences containing the likely variants.
3) Given neo K-mers assembled into likely variants, convert them into the factor graph variant format, and incrementally update a K-mer index to contain these variants.

Further embodiments allow for approximate, or "fuzzy," K-mer searches, where given a particular K-mer, all similar K-mers are identified in a data structure and data about the similar K-mers are retrieved. Approximate K-mer searches can be used for primer design, where ensuring capture of certain sequences is important (e.g., cancer testing/screening). Additionally, the approximate K-mers can be used to design targets for CRISPR-Cas9 modification of the genome.

Additional embodiments allow for the indexing of single-cell data. As science progresses, single-cell sequencing is becoming important to understand what a particular cell in a human body is doing at a particular time. Indexing K-mers for a cell at a particular timepoint can create a snapshot of what cellular processes are being performed at that time.

More embodiments allow for variant calling from the K-mer data stored within a data structure, by identifying K-mers located at a specific location versus the K-mer stored in a data structure for that same location.

Exemplary Embodiments

Many embodiments will allow scalability, efficiency, and potential for novel analysis and visualization tools that can be built upon data structures of some embodiments. Accordingly, these data support the various embodiments of the invention as described.

Approximate K-Mer Search for Specific K-Mers

A number of embodiments allow for an approximate K-mer search. In an exemplary embodiment, one implementation supports one million queries per second on a single thread, making it possible to query not just a particular K-mer, but all nearby K-mers differing by a few base pairs.

Methods: Initially, all 20-mers in GRCh38 were indexed and stored each 20-mer's location in GRCh38 using the metadata field of a data structure embodiment. The 20-mer "GGGCACCACCACACTATCTT" was used as a query against the 20-mers in the data structure, which generated a list of all 193 K-mers within a Hamming distance of 3 along with each of their locations in GRCh38 (stored as metadata in the data structure).

Figures 9A, 9B:
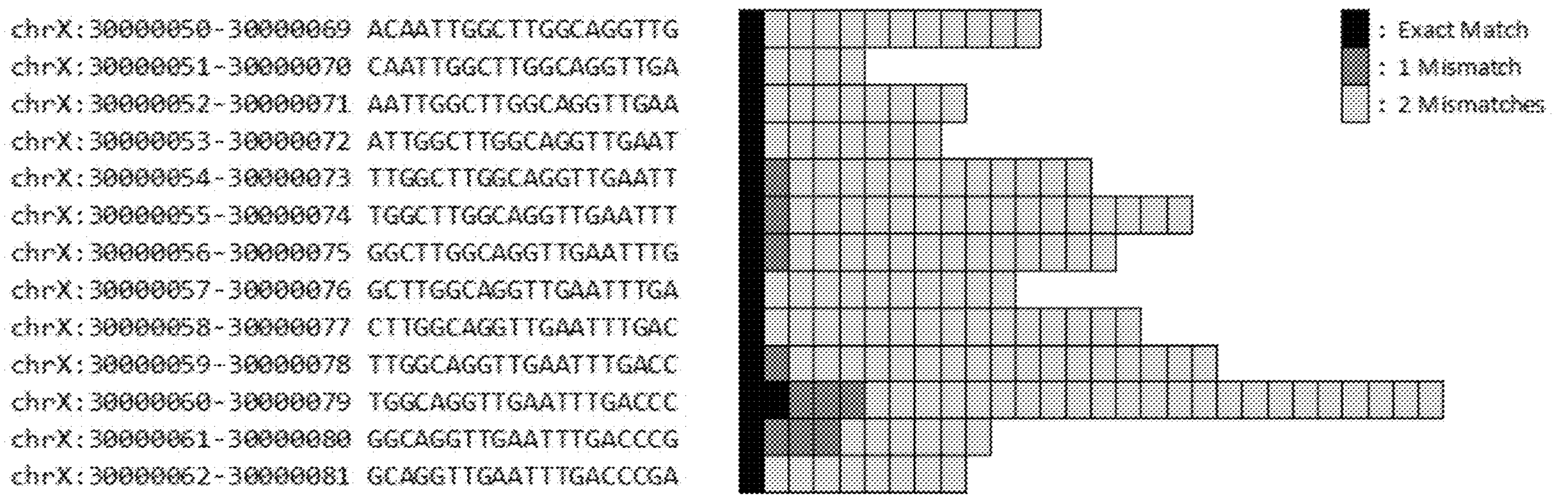
FIG. 9A illustrates output of an approximate K-mer search in accordance with various embodiments.
FIG. 9B illustrates a bar chart showing the number of matches and approximate matches of various K-mers identified by a range of genomic positions in accordance with various embodiments.

Results: The indexing process took approximately 4 minutes on 32 threads. The query took only a few milliseconds to return data on only one thread. An abbreviated table of the results of the K-mer query are illustrated in FIG. 9A, where locations of K-mers along with the number of mismatches present are illustrated.

Conclusion: The approximate K-mer search feature is further extensible to other kinds of metadata that might in the future be associated with each K-mer, like the set of known variants associated with it.

Approximate K-Mer Search for a Range of K-Mers

A number of embodiments allow for an approximate K-mer search (e.g., "fuzzy" K-mer search) of a range of K-mers. In an exemplary embodiment, one implementation supports a query for a range of K-mers and identifies similar K-mers elsewhere in the data structure, thus genome. For example, given a range of interest, one may want to identify K-mers with very few nearby Hamming neighbors.

Methods: Initially, all 20-mers in GRCh38 were indexed and stored each 20-mer's location in GRCh38 using the metadata field of a data structure embodiment. Next, the region chrX:30000050-30000062 was selected and then used as a query for a set of approximate K-mers for each K-mer whose left endpoint is in this region of interest.

Results: As seen in FIG. 9B, the 13 K-mers starting in the region of interest are illustrated along with a bar chart showing how many similar K-mers exist for each K-mer in this region. As expected, each K-mer possessed at least one exact match (representing the queried K-mer). The bar chart further illustrates how many similar K-mers exist for each queried K-mer with the number of mismatches in the returned K-mer. All queried K-mers had multiple returns with 2 mismatches, while a few returned K-mers with a single mismatch, and one K-mer returned a second, exact match.

Conclusion: Many embodiments can be used to identify how many similar regions, which could be useful for designing primers and/or genomic probes.

Developing Representations of Structural Variations and Phase Information

Some embodiments will extend the data structures to handle more complicated classes of variations: structural variations like translocations and inversions, haplotypes, and copy number variations. A goal of many embodiments is not to reinvent structural variants in terms of K-mers, but to demonstrate how representation of pan-genomic representation can be extended to include new kinds of variants in anticipation of novel contributions by external groups. A flexible pan-genomic representation will provide easy access to other researchers, facilitate adoption in the community and encourage data sharing.

Methods: Embodiments will describe structural variations in terms of their K-mer content, an approach developed in the context of structural variation (SV) detection in sequencing data by BreaKmer. (See Abo R P, Ducar M, Garcia E P, Thorner A R, Rojas-Rudilla V, Lin L, Sholl L M, Hahn W C, Meyerson M, Lindeman N I et al.: BreaKmer: detection of structural variation in targeted massively parallel sequencing data using kmers. Nucleic Acids Res 2015, 43 (3): e19; the disclosure of which is incorporated herein by reference in its entirety.). This is a subtler task than what is observed in short variations (e.g. the insertion in FIG. 2); namely, it may be useful to define a variant like a long deletion in terms like "deletion of the third exon in TP53," rather than in terms of the precise location of the deletion's start and end points. An ability to accommodate this sort of imprecision in the definition of a variant is useful because: 1) the exact breakpoint position is often less significant (e.g. clinically) than the fact of the deletion; 2) the exact breakpoint might be hard to resolve with a single rare K-mer that spans it, while the fact of the break is easier to resolve due to the observation of many pairs of K-mers on opposite sides of the break. In this case, embodiments can define this deletion as a variant with the metadata: "Some K-mer from intron 2 of TP53 and some K-mer from intron 3 of TP53 within distance A of each other" where Δ is chosen to be small relative to the length of exon 3 of TP53. The coordinates of both the deletion and of TP53 will vary from genome to genome, but a variant thus defined is potentially relevant in many genomes, and can be searched using the efficient K-mer index.

An additional embodiment will extend our factor graph approach to represent haplotype/phasing information. One potential approach is to add haplotype to the metadata of K-mers derived from a sequencing sample of linked reads or long reads, permitting subsequent filtering of K-mers that share the same haplotype ID. Another approach is to add a haplotype kind of node to our factor graph. Another approach in certain embodiments includes defining a variant as a collection of co-occurring K-mers plus metadata. Some embodiments will further define a haplotype as a collection of co-occurring variants plus metadata.

Figure 10A:
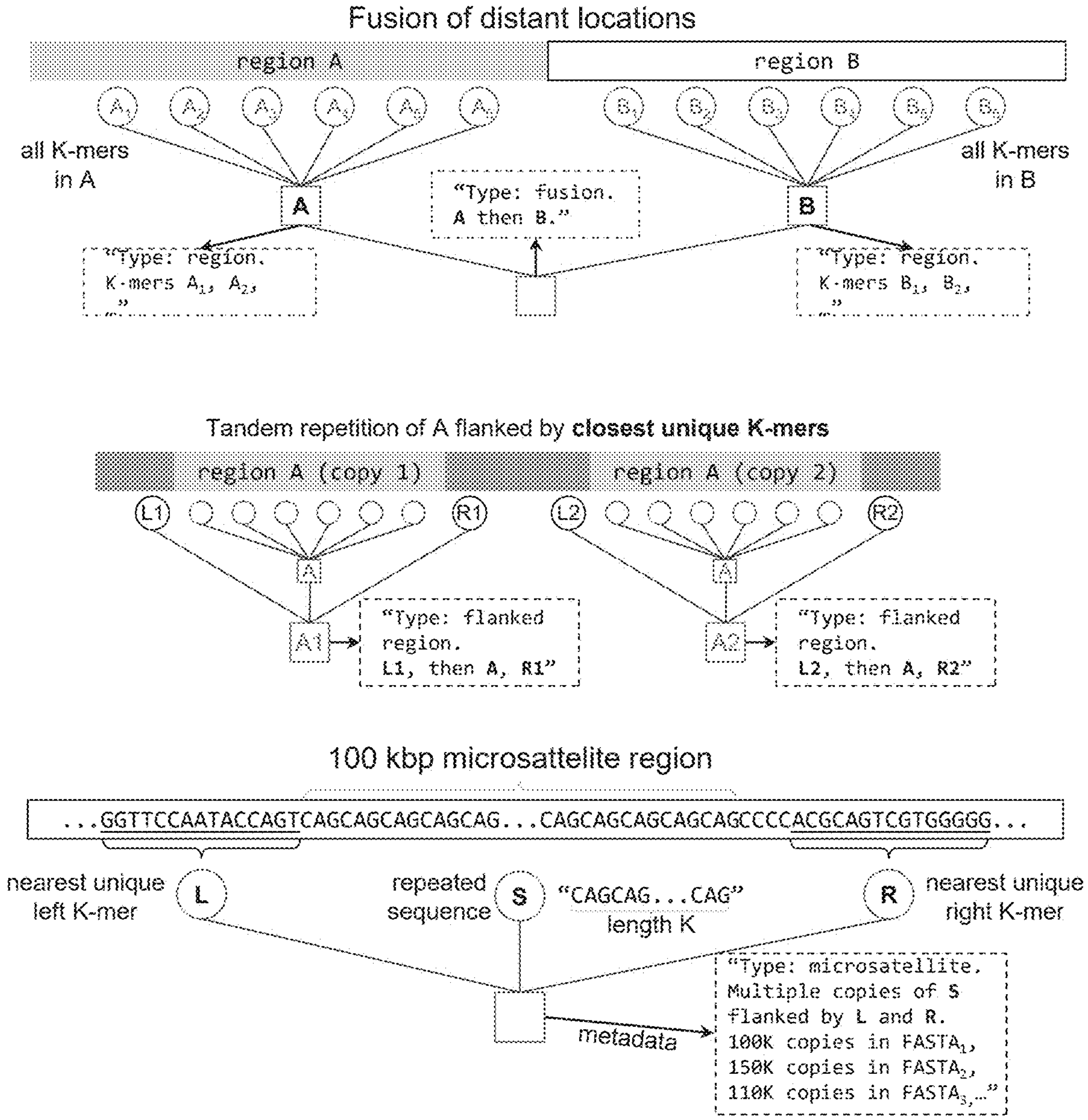
FIG. 10A illustrates the effects on K-mer content of several structural variations in accordance with various embodiments.

Results: Providing an added benefit, variants defined in terms of their K-mer effects leverage the speed and efficiency of our fast K-mer-based index. FIG. 10A illustrates the effects on K-mer content of several structural variations (a long deletion, a duplication, and a translocation). For instance, in a deletion/duplication/translocation event, the K-mer pair (k3, k9) are found in close proximity in a paired read or a single read.

Figure 10B:
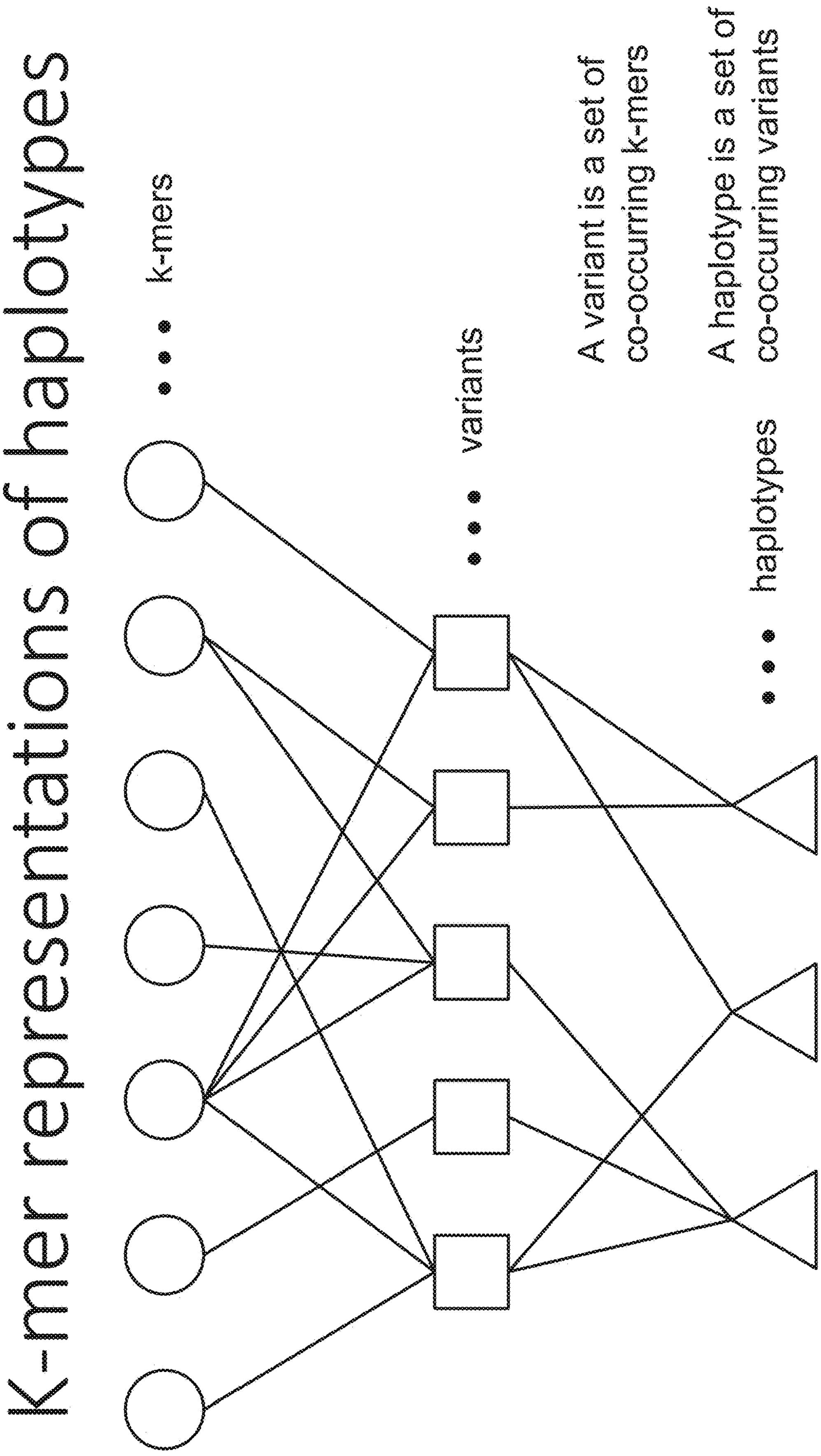
FIG. 10B illustrates haplotype information that can be included as metadata in accordance with various embodiments.

Haplotype information can be included as metadata in a data structure as shown in FIG. 10B.

Conclusion: This K-mer-based representation of structural variation permits analysis at the population level, since the precise coordinates of a variant vary by individual, permitting queries like "what fraction of indexed genomes have this long deletion?"

Defining structural variations and haplotypes without reference to the coordinates of a single reference genome enables more rapid annotation to population genomic studies.

Analyzing Variation at the Population Scale

Certain embodiments have the potential to compactly represent and efficiently compute population-scale genetic variation.

Methods: In one embodiment, 30-mers in six whole-genome sequencing samples were indexed. Then, joint K-mer counts were produced across the six samples. A variety of K-mers were queried across the sample and are illustrated in FIG. 11. A histogram was generated to illustrate the h-index of the samples, where each K-mer was treated as an "author," the samples were treated as "publications," and the K-mer count in a sample was treated as a "citation count" of that "publication." The counts were railed at 255.

Results: In FIG. 11, the queried K-mers are illustrated based on their sequence on the left column. The six columns starting headed with SRR represent each of the six input samples. The numbers in each column represent the number of counts of that K-mer in each of the samples. To illustrate the computing advantages of the present system, FIG. 11 was generated at a rate of about 1 million K-mers per second, and the histogram was computed in about eight seconds for the first $10^7$ 30-mers, namely the 30-mers that occurred at least twice in one of the six samples. The histogram illustrates that many of the K-mers from the samples are novel to the specific sample, while fewer K-mers exist in all six samples.

Conclusion: Efficient iteration through all samples jointly is possible because K-mer indexes in accordance with many embodiments is sorted and supports fast querying. Additionally, the pan-genome representation capabilities of certain embodiments (including the association with metadata), many embodiments will allow for the computation of population-wide statistics, such as the prevalence of a particular variant in a population.

Generating Rapid Visualizations of Data

Figure 12:
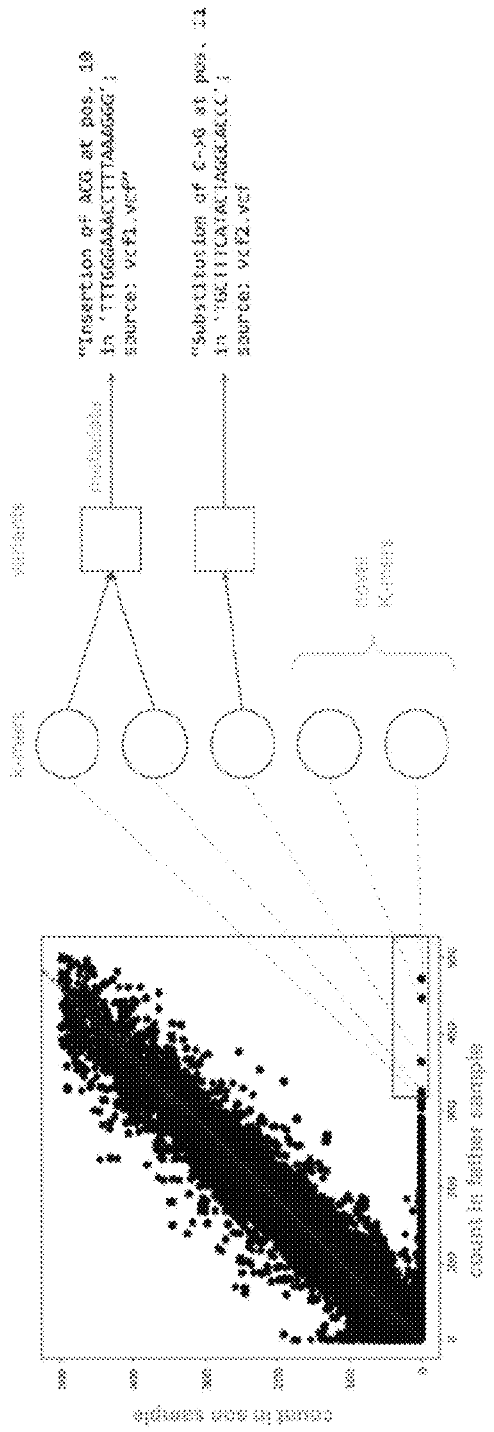
FIG. 12 illustrates K-mer counts in a father-son duo, including novel K-mers that exist in only one sample in accordance with various embodiments.

The ability to jointly query K-mer statistics enables rapid visualizations like FIG. 12, wherein each dot corresponds to a single 20-mer located at coordinates (count in father, count in son) for the father and son pair from the Genome-in-a-Bottle data. By storing metadata associated with each K-mer beyond just its count, one can use these visualizations to dive deeper into analyzing population-scale variation. As illustrated, one embodiment used already-existing functionality of iterating through multiple K-mer indexes to produce the subplot on the left in FIG. 12.

In FIG. 12, a scatter plot of all 20-mer counts in primary sequencing data for the Ashkenazim father and son. The boxed region of interest shows a set of 20-mers over-represented in the father relative to the son. Some 20-mers in the region of interest are associated with some previously-indexed variants; some 20-mers are novel.

Conclusion: The subplot on the right in FIG. 12 demonstrates planned functionality of querying known variants by visual region of interest in a K-mer scatterplot. The functionality shown in FIG. 12 permits searching for particular variants in a sequencing sample or an assembled genome. We would scan all K-mers in a file, using a K-mer index in accordance with some embodiments to look up and retain any and all variants associated with those K-mers.

Genomic Analysis Using a K-Mer Index

Figure 13A:
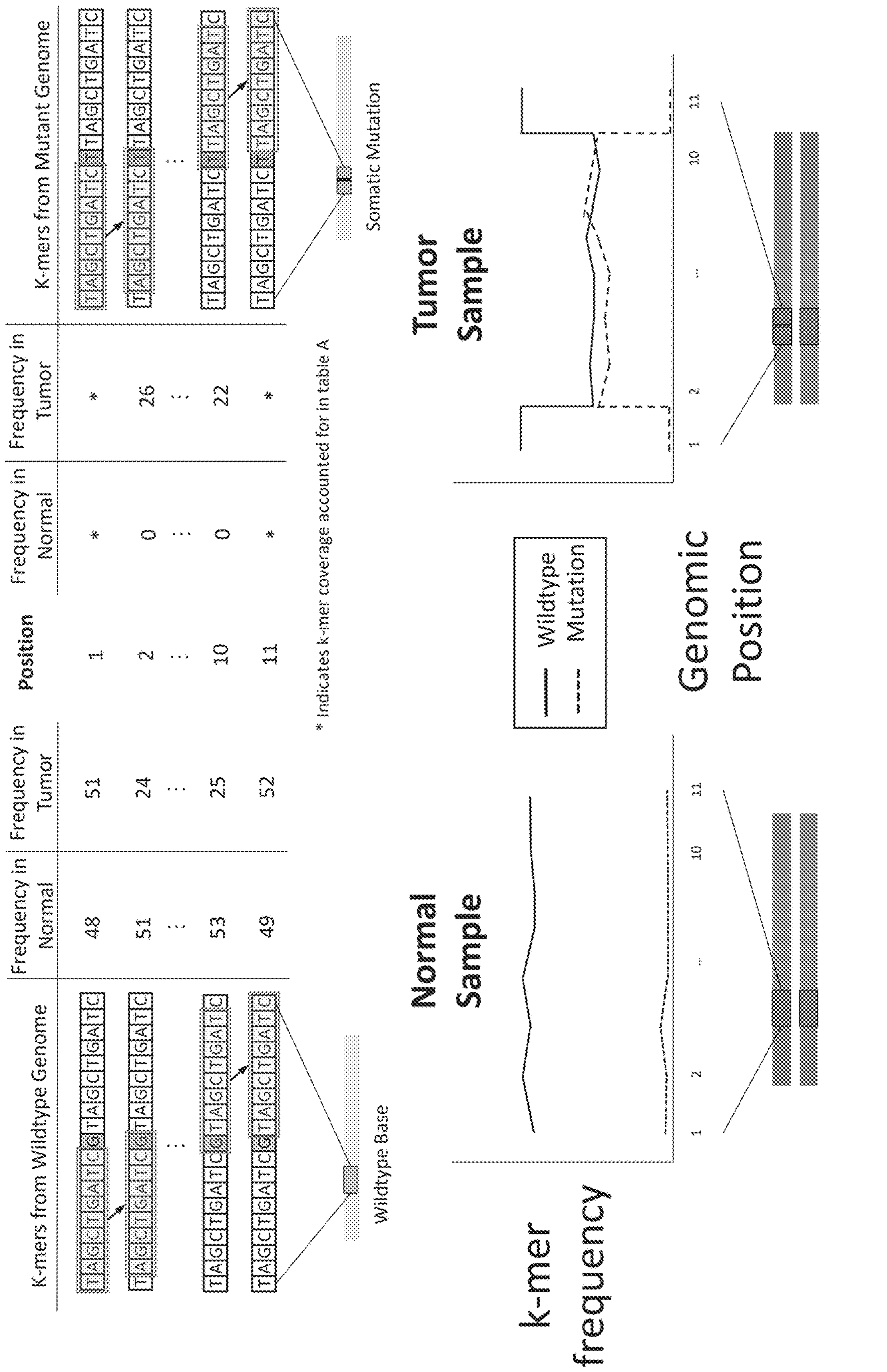
FIGS. 13A-13B illustrate mutation detection using K-mers in accordance with various embodiments.

The counts of any given K-mer from two related samples, such as a matched normal-tumor pair, provides a means to identify somatic mutations. Presumably, any somatic mutation (i.e. cancer-related) should generate a set of novel K-mers not observed in the reference or matched wildtype genome. Thus, one can use these "neo K-mers" to identify mutation events in cancer. For instance, for a given K-mer, a substitution (e.g. G to T) will generate 10 neo 10-mers (FIG. 13A). The same principle applies to indels with the number of K-mers corresponding to indel size. These cancer-related neo 10-mers will generally not be observed in "normal" germline genomes.

Figure 13B:
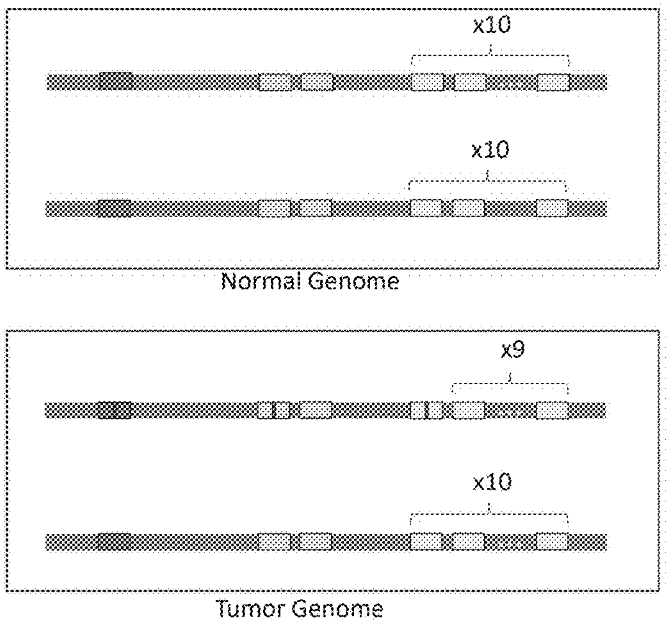

Another important respect of neo K-mers is their uniqueness for any given human genome. As seen in FIG. 13B, unique K-mers, appearing only once in the human genome including its reverse complement, provide a distinct sequence signal compared to non-unique K-mers. Therefore, the portion of unique K-mers present in a given human genome is critical for this approach. The length of a K-mer affects the fraction of unique K-mers. In general, larger K-mers have a higher chance of being unique. However, we determined that there is not much gain in the fraction of unique K-mers by increasing length (FIG. 13B). Specifically, longer K-mers are prone to having sequencing errors which leads a decrease in true unique K-mers. When one considers the 20-mers present in GRCh38, the vast majority are unique (93.8%). This property of 20-mers facilitates the efficiency of K-mer indexing for somatic variation.

Moreover, we showed that K-mer counting enables mutation discovery compared to read counts. For this demonstration we used exome sequencing data from TCGA. We examined the distribution of K-mer counts around variants that were identified from four variant callers; Mutect2, MuSE, SomaticSniper, and VarScan2. The number of validated mutations based on unique somatic K-mer counts versus wildtype K-mer counts had a highly significant correlation with Mutect2 ($R^2$=0.959, p-value<0.01) which is considered to be the gold-standard for somatic variant detection. Thus, K-mers can be readily used for somatic mutation discovery. In addition, K-mer analysis can be applied to sequencing data of any read length, thus we can use data from Oxford Nanopore and Pacific Bioscience sequencers.

Storing and Accessing Data in a Data Structure

Introduction: This exemplary embodiment illustrates how data is stored and accessed in a data structure.

Methods: This embodiment shows various means based on specific notation, parameters, and derived parameters.

Notation:

- k—K-mer size
- X—alphabet (e.g., for DNA, X={A,C,G,T})
- |X|—alphabet size (e.g., for DNA, |X|=4)
- $X^k$—the set of K-mers over alphabet X (e.g., for DNA, $|X^k|=4^k$
- ceil—ceiling function (e.g., ceil(4.1)=5; ceil(10)=10)
- $\log_2$—logarithm base 2
- div(x,L), rem(x,L)—integer-valued quotient and integer-valued remainder, respectively upon dividing integer x by integer L Data Structure Parameters:

- Integer k (K-mer size)
- Alphabet X (e.g. {A,C,G,T})
- Integer U relatively prime to $|X^k|$ (that is, U and $|X^k|$ have no factors in common) and in the set $\{1, 2, \ldots, |X^k|\}$. U is used to hash K-mers.
- Integer L in the set $\{1, 2, \ldots, |X^k|\}$. L is the number of K-mers with the same home slot (see definition of home slot below). If L==1, then each K-mer has its own slot (and the data structure would use a lot of space, so typically L is larger). L does not need to be a power of 2 or of |X|.
- Integer H, the maximum number of hash collisions before an overflow is declared (also known as "reprobes")
- Trait-like parameters allowing for multiple possible behaviors of the data structure depending on their values:
  - Boolean value IsSorted—controls whether all entries are sorted (in hash order) in the hash table or not
  - Boolean value AllowDuplicates—controls whether multiple copies of the same key (K-mer) can be in the hash table Derived Parameters:

- Integer V, the multiplicative inverse of U modulo $|X^k|$ in the set $\{1, 2, \ldots, |X^k|\}$. V exists and is unique (thanks to Bezout's identity and the extended Euclidean algorithm). V is used to invert the hashing of K-mers.
- Integer b, the number of bits per slot in the hash table. Must satisfy $b \geq \mathrm{ceil}(\log_2(H\,L+1))$.
- Integer n, the number of slots in the hash table. Must satisfy $n_{slots} \geq \mathrm{ceil}(|X^k|/L)+H$ Defining the data structure: Let T denote the hash table. The n slots of T are addressed by the integers $\{0,1, \ldots, n-1\}$. Let T[q] denote the value stored at address q in T. Since b bits are used per slot, then $T[q] \in \{0,1, \ldots, 2^b-1\}$.

Let x and y denote K-mers, and let underlines denote hashed K-mers, e.g. $\underline{x}=U*x \pmod{|X^k|}$. To unhash a hashed K-mer $\underline{x}$, compute $x=V*\underline{x} \pmod{|X^k|}$.

A slot q is "empty" if T[q]==0. If a slot q is not empty, then let $\underline{x}_q=(q+1)*L-T[q]$ be the hashed K-mer (key) associated with this slot and its contents. The unhashed K-mer associated with this slot and its contents is $x_q=V*\underline{x}_q \pmod{|X^k|}$.

The "home slot" of (hashed) K-mer x is the unique non-negative integer q satisfying the equation: x=q L+r, with r in $\{0,1, \ldots, L-1\}$. That is, q is the quotient, and r the remainder upon division of $\underline{x}$ by L.

Inserting an element into the data structure: For a hash table (with parameters IsSorted==false and AllowDuplicates==false), to insert a K-mer key x into the table, first hash x to obtain $\underline{x}=U*x \pmod{|X^k|}$, then compute the home slot q and remainder r, and then find the smallest integer h in the set $\{1, 2, \ldots, H\}$ such that either $\underline{x}_{q+h-1}==\underline{x}$ or slot q+h−1 is empty, assuming h exists. In the first case ($\underline{x}_{q+h-1}==\underline{x}$), x is already in the table and there is nothing to do. In the second case (empty slot), assuming h exists, write T[q+h−1]←h*L−r to this slot. If h does not exist, then signal that an overflow occurred, and write x to an overflow table stored separately (possibly implemented as some other hash table). Note that h is the number of hash collisions resolved to store x in the table.

Exemplary code for inserting an element includes:

Inputs: hash table T, K-mer x

Outputs: 1) address at which x was inserted into T, 2) a Boolean signal denoting whether overflow occurred (e.g., too many hash collisions occurred)

```
def insertkey(T, x):
  x ← U * x (mod |X|·)            # hash x
  q ← div(x, L)                   # quotient upon division by L
  r ← rem(x, L)                   # remainder upon division by L
  for h in 1 to H:                # at most H hash collisions
    if T[q] == 0:                 # if slot is empty
      T[q] ← h * L − r            # write key to table
      return (q, false)           # no overflow
    else:                         # slot is occupied
      y ← (q + 1) * L − T[q]      # hashed k-mer stored in slot
      if y == x:                  # key is already in the hash table
        return (q, false)         # no overflow
    q ← q + 1                     # move to next slot
  return (q, true)                # overflow occurred
```

If an overflow occurs, then x is stored in an overflow table.

Exemplary code for reading an element includes:

Inputs: hash table T, K-mer x

Outputs: 1) address at which x is in T, 2) a Boolean signal denoting whether x is in T (output 1 is undefined if this signal is false), 3) a signal denoting whether overflow occurred (e.g., too many hash collisions occurred)

```
def locatekey(T, x):
  x ← U * x (mod |X|·)            # hash x
  q ← div(x, L)                   # quotient upon division by L
  r ← rem(x, L)                   # remainder upon division by L
  for h in 1 to H:                # at most H hash collisions
    if T[q] == 0:                 # if slot is empty
      return (q, false, false)    # x not in table
    else:                         # slot is occupied
      y ← (q + 1) * L − T[q]      # hashed k-mer stored in slot
      if y == x:                  # key is already in the hash table
        return (q, true, false)   # no overflow
    q ← q + 1                     # move to next slot
  return (q, false, true)         # overflow occurred
```

If an overflow occurs, then check the overflow table for x.

Associating metadata with a K-mer: The insertkey and locatekey operations return the address at which K-mer x is either inserted or located. This address can be used to index into an external table or other data structure that stores metadata. If an overflow occurs, then K-mer metadata is written to an external metadata overflow table (perhaps implemented as a hash table).

Other Possible Behaviors:

- If IsSorted==true, then modify the above so that a key x may eject a key y previously stored in a slot if x<y, forcing y to move one slot to the right (forcing all occupied slots to the right of y to also shift one slot to the right until an empty slot is found and occupied). A k-mer that moves more than H slots from its home slot overflows (is ejected from the hash table) and is placed into the overflow table. Sortedness enables operations on multiple hash tables to be computed more quickly (like computing a union or intersection of two tables).
- If AllowDuplicates==true, then modify the above so that a key x may occur multiple times in the table. This can be accomplished by continuing the insertkey operation until an empty slot is found, without checking whether x is already in the table.

Doctrine of Equivalents

Having described several embodiments, it will be recognized by those skilled in the art that various modifications, alternative constructions, and equivalents may be used without departing from the spirit of the invention. Additionally, a number of well-known processes and elements have not been described in order to avoid unnecessarily obscuring the present invention. Accordingly, the above description should not be taken as limiting the scope of the invention.

Those skilled in the art will appreciate that the presently disclosed embodiments teach by way of example and not by limitation. Therefore, the matter contained in the above description or shown in the accompanying drawings should be interpreted as illustrative and not in a limiting sense. The following claims are intended to cover all generic and specific features described herein, as well as all statements of the scope of the present method and system, which, as a matter of language, might be said to fall therebetween.

What is claimed is:

1. A method for indexing K-mers, comprising:

obtaining a nucleotide sequence;

defining a K-mer size; and indexing K-mers of the nucleotide sequence according to the K-mer size, wherein each K-mer represents a sequence segment of the nucleotide sequence; wherein each sequence segment comprises a prefix portion and a remainder portion, wherein the prefix portion is defined a prefix value and the remainder portion is defined by a remainder value;

wherein the K-mers are stored in a data structure defined by a plurality of slots, wherein each slot has an address and stores data, the address is defined by the prefix value of each K-mer, and the slot stores the remainder value, wherein indexing the K-mers comprises Fibonacci hashing to compute the prefix value and the remainder value of each K-mer;

wherein indexing the K-mers comprises linear hash-collision resolution when a slot is already filled by a K-mer sharing the same prefix value.

2. The method of claim 1, wherein the data structure further includes metadata associated with each K-mer stored therein.

3. The method of claim 2, wherein the metadata comprises at least one of the following: source, population, species, date of acquisition, sequencing platform, data type, and identity of the sample.

4. The method of claim 1, further comprising updating the data structure with additional sequence data.

5. The method of claim 4, wherein the updating step is accomplished by:

obtaining additional sequence data; and indexing K-mers in the additional sequence data according to the K-mer size, wherein the K-mers are stored in the data structure.

6. The method of claim 1, wherein the nucleotide sequence is a whole genome sequence.

7. The method of claim 1, wherein the nucleotide sequence is a human reference sequence.

8. The method of claim 1, wherein the K-mer size is 11-150 base pairs.

9. The method of claim 1, wherein each K-mer is stored as a binary integer representing the DNA sequence of the sequence segment of each K-mer.

10. The method of claim 9, wherein the K-mers are converted to generate a more uniform distribution via the Fibonacci hashing.

11. The method of claim 10, wherein the Fibonacci hashing comprises multiplying each K-mer by u(mod B), where B is a table size of the data structure, and u is any number with no common divisors with B.

12. The method of claim 11, further comprising retrieving at least one K-mer from the data structure.

13. The method of claim 12, wherein the retrieved K-mer is unhashed from the data structure by multiplying each K-mer by v(mod B), where v*u*x=x(mod B), where x represents the binary integer representing the underlying DNA sequence of the sequence segment of the K-mer.

14. The method of claim 1, wherein the linear hash collision resolution comprises scanning to a lower order slot and incrementing the remainder value a value equal to a difference between the prefix and the lower order slot.

15. The method of claim 1, wherein indexing the K-mers comprises storing the remainder value of a K-mer in another data structure when exceeding a maximum number of hash collisions.

16. A data structure for storing genetic or genomic data, comprising:

a plurality of memory slots and a plurality of K-mers, wherein each K-mer represents a sequence segment of a nucleotide sequence, wherein each sequence segment comprises a prefix portion and a remainder portion, wherein the prefix portion is defined a prefix value and the remainder portion is defined by a remainder value, wherein each memory slot is associated with an address, wherein each K-mer is stored in a specific memory slot based on the prefix value of the K-mer, and the remainder value is stored in the memory slot, wherein the prefix value and the remainder value of each K-mer are yielded by a Fibonacci hash function, wherein the remainder value of a subset of K-mers comprise an increment or a decrement corresponding to a linear hash-collision resolution.

17. A method to identify genomic events, comprising:

accessing a data structure, wherein the data structure comprises a plurality of memory slots and a plurality of K-mers, wherein each K-mer represents a sequence segment of a nucleotide sequence, wherein each sequence segment comprises a prefix portion and a remainder portion, wherein the prefix portion is defined a prefix value and the remainder portion is defined by a remainder value, wherein each memory slot is associated with an address, wherein each K-mer is stored in a specific memory slot based on an integer value of the prefix value of the K-mer, and the remainder value is stored in the memory slot, wherein the prefix value and the remainder value of each K-mer are yielded by a Fibonacci hash function, wherein the remainder value of a subset of K-mers comprise an increment or a decrement corresponding to a linear hash-collision resolution;

querying the data structure to obtain a set of K-mers associated with a genomic event; and outputting the set of K-mers associated with the genomic event.

* * * * *